(12) United States Patent
Regittnig et al.

(10) Patent No.: US 11,454,616 B2
(45) Date of Patent: Sep. 27, 2022

(54) DETERMINING ENRICHMENTS OF TRACERS OF GLUCOSE BY MASS SPECTROMETRY

(71) Applicant: Medizinische Universität Graz, Graz (AT)

(72) Inventors: Werner Regittnig, Graz (AT); Harald Köfeler, Stattegg (AT); Martin Trötzmüller, Nestelbach (AT); Alexander Triebl, Trausdorf (AT)

(73) Assignee: Medizinische Universität Graz, Graz (AT)

( * ) Notice: Subject to any disclaimer, the term of this patent is extended or adjusted under 35 U.S.C. 154(b) by 361 days.

(21) Appl. No.: 16/624,841

(22) PCT Filed: Jun. 22, 2018

(86) PCT No.: PCT/EP2018/066759
§ 371 (c)(1),
(2) Date: Dec. 19, 2019

(87) PCT Pub. No.: WO2019/002127
PCT Pub. Date: Jan. 3, 2019

(65) Prior Publication Data
US 2020/0217828 A1    Jul. 9, 2020

(30) Foreign Application Priority Data
Jun. 27, 2017 (EP) ..................................... 17178182

(51) Int. Cl.
*G01N 30/72* (2006.01)
*G01N 33/58* (2006.01)
(Continued)

(52) U.S. Cl.
CPC ............ *G01N 30/72* (2013.01); *G01N 33/583* (2013.01); *G01N 33/66* (2013.01); *G01N 2030/8836* (2013.01)

(58) Field of Classification Search
CPC .... G01N 30/72; G01N 33/583; G01N 33/665; G01N 2030/8813; G01N 2030/8836; H01J 49/0027; H01J 49/0031; H01J 49/0036
See application file for complete search history.

(56) References Cited

U.S. PATENT DOCUMENTS

2013/0103337 A1    4/2013 Eller

FOREIGN PATENT DOCUMENTS

KR    101311412 B1    9/2013
WO    2007031717 A1    3/2007
(Continued)

OTHER PUBLICATIONS

Toffolo et al, "Glucose Fluxes During OGTT in Adolescents Assessed by a Stable Isotope Triple Tracer Method", Journal of Pediatric Endocrineology & Metabolism, 21, 31-45, 2008 (Year: 2008).*

(Continued)

*Primary Examiner* — David E Smith
(74) *Attorney, Agent, or Firm* — Robert A. Blaha; Smith Tempel Blaha LLC (57) ABSTRACT

Provided is a method for determining, in a sample, enrichments of a first and a second stable-labeled tracer of a target substance including glucose, the first tracer and the second tracer having the same or similar chemical structure as the target substance, the method including: ionizing the first tracer, the second tracer and the target substance of the sample; measuring intensities of ions deriving from the target substance, the first tracer and the second tracer using a mass analyzer; calculating an enrichment of the first tracer (Continued)

from a first ratio of intensity of the ions deriving from the first tracer to the intensity of the ions deriving from the target substance employing a first calibration curve independent of enrichments of each of the second tracer; wherein the mass analyzer is operated so as to resolve an ion peak deriving from a tracer and having a width $\Delta(m/z)$ at half maximum peak height equal to or smaller than $1 \times 10^{-2}$.

18 Claims, 5 Drawing Sheets

(51) Int. Cl.
    *G01N 33/66*     (2006.01)
    *G01N 30/88*     (2006.01)

(56) References Cited

FOREIGN PATENT DOCUMENTS

| WO | 2007106816 A2 | 9/2007 |
|---|---|---|
| WO | 2011084751 A1 | 7/2011 |
| WO | 2014105858 A1 | 7/2014 |
| WO | 2016141204 A1 | 9/2016 |

OTHER PUBLICATIONS

Xia et al, "Use of Electrospray Ionization Ion-Trap Mass Spectrometry and Principal Component Analysis to Directly Distinguish Monosaccharides", Rapid Commun. Mass Spectrom. 2012, 26, 1259-1264 (Year: 2012).*
Haidar et al, "Validity of Triple and Dual-Tracer Techniques to Estimate Glucose Appearance", Am. J Physicol. Endocrinol. Meta 302, E1493-E1501. 2012 (Year: 2012).*
Basu et al, "Use of a Novel Triple-Tracer Approach to Assess Postprandial Glucose Metabolism", Am J. Physiol. Endocrinol. 284 E55-E69, 2003 (Year: 2003).*
Haidar et al, "Validity of Triple and Dual-Tracer Techniques to Estimate Glucose Appearance", Am. J Physicol. Endocrinol. Meta 302, E1493-E1501. 2012 (Year: 2013).*
Toffolo et al, "Glucose Fluxes During OGTT in Adolescents Assessed by a Stable Isotope Triple Tracer Method", Journal of Pediatric Endocrinology & Metabolism, 21, 31-45, 2008 (Year: 2008).*
Toffolo, G. et al. „Glucose Fluxes During OGTT in Adolescents Assessed by a Stable Isotope Triple Tracer Method; Journal of pediatric endocrinology and metabolism, vol. 21, No. 1, Jan. 1, 2008; pp. 31-45.
Basu, R. et al. „Use of a novel triple-tracer approach to assess postprandial glucose metabolism; American Journal of Physiology: endocrinology and metabolism; vol. 284, No. 1, Jan. 1, 2003; pp. E55-E69.
Haidar, A. et al. „Validity of triple- and dual-tracer techniques to estimate glucose appearance; American Journal of Physiology: Endocrinology and Metabolism, vol. 302, No. 12, Mar. 27, 2012; pp. E 1493-E1501.
Danzer et al., Guidelines for Calibration in analytical Chemistry; Part 2. Multispecies Calibration (IUPAC Technical Report); Pure and Applied Chemistry, vol. 76, No. 6, pp. 1215-1225, 2004.
Rizza, R. A. et al., "Accurate Measurement of Postprandial Glucose Turnover: Why is it difficult and how can it be done (Relatively) simply?"; Diabetes; vol. 65, May 2016; pp. 1133-1145.
Xia, B. et al., "Use of electrospray ionization ion-trap tandem mass spectrometry and principal component analysis to directly distinguish monosaccharides"; Research Article; Rapid. Commun.; Mass Spectrom; Mar. 6, 2012; 26, pp. 1259-1264.

Bereman, M. S. et al., "Carbohydrate Analysis by Desorption Electrospray Ionization Fourier Transform Ion Cyclotron Resonance Mass Spectrometry"; Analytical Chemistry, vol. 79, No. 22, Nov. 15, 2007, pp. 8812-8815.
Herath, K. B. et al., "Determination of low levels of $^2$H-labeling using high-resolution mass spectrometry: Application in studies of lipid flux and beyond"; Research Article, Rapid. Commun., Mass Spectrom 28, Oct. 27, 2013, pp. 239-244.
Llchenko, S. et al., "An Improved Measurement of Isotopic Ratios by High Resolution Mass Spectrometry"; J Am Soc Mass Spectrom, Feb. 2013; pp. 1-9.
Kamphorst, J.J. et al., "Liquid chromatography—high resolution mass spectrometry analysis of fatty acid metabolism"; Analytical Chemistry, Dec. 1, 2011, pp. 1-18.
Du et al., "Trace glucose fluxes in individuals with prediabetes using stable isotopes"; Chinese Medical Journal, 2014, 127, pp. 1726-1731.
Borno, A. et al. „Glucose and glycerol concentrations and their tracer enrichment measurements using liquid chromatography tandem mass spectrometry: LC-MS/MS measurements of glucose and glycerol; Journal of mass spectrometry; Vo. 49, No. 10, Sep. 29, 2014, pp. 980-988.
Frey,A. J. et al. „LC-quadrupole/Orbitrap high-resolution mass spectrometry simultaneous quantification and13C-isotopic labeling of acyl-coenzyme A thioesters; Analytical and Bioanalytical Chemistry, Springer, DE, vol. 408, No. 13, Mar. 11, 2016; pp. 3651-3658.
Sun, D. et al. „Quantification of the concentration and ^1 ^3C 1 3C tracer enrichment of long-chain fatty acyl-coenzyme A in muscle by liquid chromatography/mass spectrometry, Analytical Biochemistry, Elsevier, Amsterdam, NL, vol. 349, No. 1, Feb. 1, 2006, pp. 87-95.
Marshall, A. G. et al. „High-resolution mass spectrometers; Annual review of analytical chemistry; vol. 1, No. 1, pp. 579-599.
Trötzmüller, M. et al. „Determination of the isotopic enrichment of 13 C-and 2 H-Labeled Tracers of glucose using high-resolution mass spectrometry: application to dual- and triple-tracer studies; analytical chemistry, vol. 89, No. 22, pp. 12252-12260.
Englyst, H.N. et al.; Classification and Measurement of Nutritionally Important Starch Fractions; European Journal of Clinical Nutrition (1992) 46 (Suppl. 2), S33-S50.
Louwagie, M. et al.; Introducing AAA-MS, a Rapid and Sensitive Method for Amino Acid Analysis Using Isotope Dilution and High-Resolution Mass Spectrometry; Journal of Proteome Research; Jun. 8, 2012; vol. 11; pp. 3929-3936; American Chemical Society Publications.
Brunengraber, D.Z. et al.; Gas Chromatography-Mass Spectrometry Assay of 18O Enrichment of Water as Trimethyl Phosphate; Analytical Biochemistry 306, Jun. 21, 2002; pp. 278-282.
Chen, Su-Hwei et al.; Derivatization-High Performance Liquid Chromatographic Determination of Methanol in Human Plasma, Journal of Liquid Chromatography & Related Technologies, 20:12, 1967-1978 (1997), DOI: 10.1080/10826079708005556.
Rosenblatt J. et al.; Stable Isotope Tracer Analysis by GC-MS, Including Quantification of Isotopomer Effects, Modeling in Physiology; American Physiological Society (1992); E584-E596.
Su, X et al.; Metabolite Spectral Accuracy on Orbitraps; Analytical Chemistry 2017, ACS Publications; vol. 89; pp. 5940-5948.
Wu, Z. et al.; Determination of Phenylalanine Isotope Ratio Enrichment by Liquid Chromatography/Time-of-Flight Mass Spectrometry; European Journal of Mass Spectrometry (2004); vol. 10, pp. 619-623.
Moran, A et al.; A Novel Triple-Tracer Approach to Assess Postprandial Protein Turnover; American Journal Physiology of Endocrinal Metabolism 315; E469-E477, 2018.

\* cited by examiner

DETERMINING ENRICHMENTS OF TRACERS OF GLUCOSE BY MASS SPECTROMETRY

TECHNICAL FIELD

The present invention relates to a method for determining enrichment levels of at least two tracers of a target substance including glucose using mass spectrometry. Further, the present invention relates to a set of molecules for determining metabolism of a target substance, in particular including glucose and further relates to a system for determining metabolism of a target substance including the set of molecules.

TECHNOLOGICAL BACKGROUND

Multiple-tracer techniques for investigating whole-body glucose fluxes usually involve the administration of several glucose tracers to the study subject and the subsequent determination of tracer enrichments in sampled blood. In many clinical studies applying these techniques, stable-labeled glucose isotopomers are used as tracers (e.g., [6,6-$^2$H$_2$]glucose, [1-$^{13}$C$_1$]glucose, [U-$^{13}$C$_6$]glucose) and the analysis of the stable isotopic tracer enrichments in blood plasma is accomplished by quadrupole-mass spectrometers (Q-MS). Typically, this low-resolution mass analyzer is coupled to gas chromatographic (GC) or liquid chromatographic (LC) separation systems and used to measure the relative intensities of selected ions deriving from unlabeled glucose molecules (tracee) and the glucose tracers. From the observed relative ion intensities, the tracer enrichments, usually expressed as tracer-to-tracee ratios (TTR), are then estimated. Because of the natural occurrence of heavier isotopes in the monitored ions (e.g., ~1.1% of carbons are $^{13}$C-atoms), heavier isotopic variants of ions deriving from the tracee will be present in the mass analyzer and may make significant contributions to the ion signal in the mass channels designated for the glucose tracers. Therefore, prior to calculating TTR values from the relative ion intensity data, it is necessary to correct the raw MS data for intensity contributions arising from naturally occurring isotopic variants of the monitored ions. Unfortunately, correction of ion intensity data for these interferences becomes considerably more complicated when two or more glucose tracers are used at once and when recycling of one or more of the adopted glucose tracers is occurring during the experiments.

Toffolo et al., Journal of Pediatric Endocrinology and Metabolism, 21, 31-45 (2008) discloses glucose fluxes assessed by a triple-tracer method, wherein three stable isotopically labeled tracers containing $^{13}$C- or $^2$H-substitutions ([6,6-$^2$H$_2$]glucose, [1-$^{13}$C$_1$]glucose, [U-$^{13}$C$_6$]glucose) were administered to human beings and blood samples were analyzed by GC-Q-MS having a low resolution. Herein, tracer enrichments were estimated from relative ion intensity data obtained by mass analysis of the pentaacetate derivatives of glucose isotopologues using the positive chemical ionization mode and selective monitoring of ions at mass-to-charge ratios (m/z) of 331 (M+0 ion), 332 (M+1 ion), 333 (M+2 ion), and 337 (M+6 ion), corresponding to tracee, [1-$^{13}$C$_1$]-, [6,6-$^2$H$_2$]-, and [U-$^{13}$C$_6$]glucose molecules, respectively. Due to the high number of carbon, hydrogen and oxygen atoms in the monitored ions (C$_{14}$H$_{19}$O$_9$), the signal intensity contributions in the M+1 and M+2 channels from isotopic variants of ions deriving from the tracee molecules are ~13.2% and ~2.5%, respectively. Thus, in this case, tracee isotopologues significantly overlap with both the [1-$^{13}$C$_1$]-, and [6,6-$^2$H$_2$]glucose tracers. In addition, ~12.4% of the ions deriving from the [1-$^{13}$C$_1$]glucose tracer appears in the M+2 channel and, hence, greatly interferes with the intensity measurement of the M+2 ions deriving from the tracer. Moreover, in this previous study, recycling of the infused [U-$^{13}$C$_6$]glucose tracer occurred via the gluconeogenesis pathway, thereby generating significant amounts of glucose isotopologues with masses of M+1, M+2, and M+3. Thus, it was necessary to also determine the signal intensity contributions in the M+1 and M+2 channels arising from the recycled glucose isotopologues. This was done by additional monitoring of M+3 ions and assuming that during tracer recycling equal amounts of M+1, M+2 and M+3 glucose isotopologues were generated. To correct the ion intensity data for all the mentioned interferences, the authors had to solve a rather complicated system of algebraic equations using matrix calculus.

The use of complex procedures for correcting ion intensity data increases the risk of introducing systematic errors (or inaccuracies) into the tracer enrichment determinations and also gives rise to additional uncertainties (i.e., random errors or imprecisions) that contribute to the spread in the final tracer enrichment results. In general, the amount of these additional imprecisions is dependent on the magnitude and number of corrections applied to the ion intensity data.

To reduce the complexity of correcting relative ion intensity data in the application of triple-tracer methods, previous studies have used a radioactive tracer (e.g., [6-$^3$H$_1$]glucose) in place of one of the three stable-labeled tracers which, however, entailed the risk of exposing the study subject to radiation hazard.

Basu et al., American Journal of Physiology Endocrinology Metabolism 248:E55-E69, 2003 discloses the determination of postprandial glucose fluxes using a triple-tracer method, wherein one radioactive glucose tracer ([6-$^3$H$_1$] glucose) and two stable-labeled glucose tracers containing $^{13}$C- or $^2$H-substitutions ([1-$^{13}$C$_1$]- and [6,6-$^2$H$_2$]glucose) were administered to human beings. Herein, the enrichment of the radioactive tracer in the sampled blood was assessed using liquid scintillation counting and that of the stable-labeled tracers were determined from relative ion intensity data obtained by GC-Q-MS analysis of the methyloxime pentatrimethylsilyl derivatives of glucose isotopologues using the electron impact mode and selective monitoring of ions at m/z of 160, 161, 319, and 321, corresponding to tracee, [1-$^{13}$C$_1$]glucose, tracee, and [6,6-$^2$H$_2$]glucose molecules, respectively. Due to the high analytical sensitivity associated with liquid scintillation counting, the radioactive tracer was infused at low rates and the amount of radioactive tracer present in the blood plasma was below the level of detection of the MS analyzer. Therefore, no spectral interference between the radioactive tracer and stable-labeled glucose tracers occurred in the MS analyzer. However, in this triple-tracer method, the achieved reduction in complexity of correcting relative ion intensity data comes at the price of exposing study subjects to radiation, and the potential hazard of radiation exposure precludes its use in human studies involving particular groups of the population, such as children or pregnant women.

A further way of reducing complexity of correcting relative ion intensity data in triple-tracer applications may be the use of highly-substituted instead of singly-substituted glucose tracers (e.g., [U-$^{13}$C$_6$; 1,2,3,4,5,6,6-$^2$H$_7$]glucose in place of [1-$^{13}$C$_1$]glucose). Thereby, ions deriving from the highly-substituted glucose tracer appear in higher mass channels and, thus, may not interfere with the intensity measurement of ions deriving from the tracers with lower masses (e.g., [6,6-$_2$H$^2$]glucose tracers). However, the significantly higher costs of highly-substituted glucose tracers may limit their use in triple-tracer studies.

Haidar et al., American Journal of Physiology Endocrinology Metabolism 302: E1493-E1501, 2012 discloses a triple stable isotope tracer method to estimate whole-body glucose fluxes, wherein a highly-substituted, a doubly $^2$H-labeled, and a uniformly $^{13}$C-labeled tracer of glucose (i.e., [U-$^{13}$C$_6$; 1,2,3,4,5,6,6-$^2$H$_7$]-, [6,6-$^2$H$_2$]- and [U-$^{13}$C$_6$]-glucose, respectively) were administered to human beings. Herein, tracer enrichments were estimated from relative ion intensity data obtained by GC-Q-MS analysis of the methyloxime pentatrimethylsilyl derivatives of glucose isotopologues using the electron impact mode and selective monitoring of ions at m/z of 319 (M+O ion), 321 (M+2 ion), 323 (M+4 ion), and 327 (M+8 ion), corresponding to tracee, [6,6-$^2$H$_2$]-, [U-$^{13}$C$_6$]-, and [U-$^{13}$C$_6$; 1,2,3,4,5,6,6-$^2$H$_7$]glucose molecules, respectively. Thereby, the ions deriving from the highly-substituted glucose tracer appeared in the M+8 channel and, thus, did not interfere with the intensity measurement of the M+2 and M+4 ions deriving from the [6,6-$^2$H$_2$]- and [U-$^{13}$C$_6$]glucose tracers with lower masses. However, as costs of the highly-substituted glucose tracer are significantly higher than those of the previously used singly-labeled glucose tracer, the reduction in complexity of correcting relative ion intensity data achieved with this method must be balanced against the increased expense of the highly-substituted glucose tracer. Furthermore, when applying this method, recycling of the highly-substituted glucose tracer occurred, thereby generating significant amounts of glucose isotopologues with masses of M+5 and M+4. Thus, ions arising from these isotopologues interfered with the intensity signals in the mass channels for the [U-$^{13}$C$_6$]glucose tracer, thereby necessitating additional corrections in the raw MS intensity data.

US 2013/0103337 A1 discloses a high-resolution mass spectrometer and methods for determining the isotopic anatomy of organic and volatile molecules, wherein a glucose mass spectrum was acquired. An isotopic composition of an analyte of a sample from a patient was analyzed by a mass spectrometer. The fragmentation of glucose was analyzed using low-resolution mass spectra.

WO 2007/031717 A1 discloses mass marker moieties capable of splitting into two or more fragments, wherein mass labels are identified by mass spectrometry.

WO 2007/106816 A2 discloses a substrate for mass spectrometric analysis including a monosaccharide, in particular D-glucose.

Isotope tracer methodology has been widely used to study various metabolic functions in human subjects. Therein, dual- or triple-tracer techniques may have been used to investigate whole-body glucose metabolism in human subjects, wherein the enrichment of stable-labeled glucose tracers may have been measured in the blood samples by low-resolution mass spectrometry (LRMS). Generally, when using LRMS, the number of ion signal interferences may rise rapidly with the number of stable-labeled glucose tracers present in the sample. Therefore, the number of stable-labeled glucose tracers that can be simultaneously employed (quantified) may have been limited to two or three, since in this case the computational effort as well as statistical imprecision and inaccuracy associated with the correction for ion signal interferences may have already increased to a maximum acceptable extent.

Thus, there may be a need for a method for determining enrichments of at least two tracers of at least one target substance including glucose, wherein the method avoids ion signal interferences and allows the tracer enrichments to be determined with high precision and accuracy as well as with low computational costs.

Furthermore, in previous studies applying multiple tracer methods, investigations into whole-body glucose metabolism may have not been performed in full detail, since the number of simultaneously employed stable-labeled glucose tracers may have been limited to two or three.

Thus, there may also be a need for a method for determining enrichments of tracers of glucose which permits more than three stable-labeled glucose tracers to be precisely and accurately determined in a blood sample, thereby facilitating more detailed investigations into whole-body glucose metabolism.

Additionally, to reduce the number of ion signal interferences in the application of previous triple-tracer methods, a stable singly-labeled tracer may have been replaced by a stable highly-substituted or a radioactive glucose tracer which, however, may have entailed higher costs or the risk of exposing the study subject to radiation hazard, respectively.

Thus, there may also be a need for a method for determining enrichments of tracers of at least one target substance including glucose which provides a greater flexibility in choosing the type and number of stable-labeled glucose tracers that can be simultaneously employed, thereby avoiding the use of costly, highly-substituted stable tracers and/or radioactive tracers.

SUMMARY

Embodiments of the present invention reduce the complexity in the conversion of mass spectrometry measured relative ion intensities to tracer enrichments, thereby lowering the computational effort and improving the precision and accuracy in the determination of multiple tracer enrichments. Furthermore, embodiments of the present invention provide a greater flexibility in choosing the type and number of stable-labeled tracers that can be simultaneously employed, thereby facilitating more detailed investigations into whole-body metabolism and avoiding the use of radioactive tracers and/or costly, highly substituted stable tracers.

According to an embodiment it is provided a method for determining, in a sample, enrichments of a first and at least one second stable-labeled tracer of at least one target substance including glucose, the first tracer and the second tracer having the same or similar chemical structure as the target substance, the method comprising: ionizing the first tracer, the second tracer and the target substance of the sample, in particular by electrospray ionization; measuring intensities of ions deriving from the target substance, of ions deriving from the first tracer and of ions deriving from the second tracer using a high-resolution mass analyzer, in particular an Orbitrap mass analyzer; calculating an enrichment of the first tracer from a first ratio of the intensity of the ions deriving from the first tracer to the intensity of the ions deriving from the target substance employing a first calibration curve being independent of enrichment levels of each of the at least one second tracer; wherein the high-resolution mass analyzer is operated so as to resolve an ion peak deriving from a tracer and having a width $\Delta(m/z)$ at half maximum peak height equal to or smaller than $1\times10^{-2}$, in particular smaller than $5\times10^{-3}$, further in particular smaller than $3\times10^{-3}$.

The enrichments of the first and the at least one second stable-labeled tracer may relate to or define in particular a respective ratio between the amount or concentration or number of ions of the respective tracer and that of the target molecule.

The method may completely be unrelated to a therapeutic or diagnostic method. In some embodiments, the sample may not originate from any living organism.

Overview of Embodiments

In other embodiments, the method may be employed for determining metabolism of a target substance, in particular including glucose. In these embodiments, the first tracer and the at least one second tracer may have been administered to a living organism in same or different forms, such as by supplying at least one of the tracers to a blood stream of the living organism and supplying at least one other tracer to a digestive tract of the living organism. The sample may originate in these embodiments from blood taken from the living organism at different points in time after administration.

The first and the at least one second stable-labeled tracer of a target substance may have been synthesized by using either isotopic or bioisosteric substitution approaches. In the isotopic substitution, one or more atoms in the parent molecule (or target substance) is substituted with an isotope which is not the most abundant naturally occurring isotope of that atom. Thus, the first and the second stable-labeled tracers may each contain exactly one isotopic substitution or may comprise more than one, for example two, three, four or even more isotopic substitutions for the same or different kinds of atoms. Preferably, each, the first and the second stable-labeled tracers contain only one isotopic substitution (exactly once) for a particular atom. The first tracer may for example have one (or two) $^{13}C$-substitutions and the second tracer may for example have one (or two) $^{2}H$-substitutions. Alternatively, the first tracer may for example incorporate (exactly) one $^{2}H$-substitution and the second tracer may for example incorporate (exactly) two $^{2}H$-substitutions. Alternatively, the first tracer may for example have (exactly) one $^{13}C$-substitution and no $^{2}H$-substitution, and the second tracer may have one $^{2}H$-substitution but no $^{13}C$-substitution. Other combinations are possible.

In contrast to the isotopic substitution, the bioisosteric substitution approach for the synthesis of the first and the at least one second stable-labeled tracer may involve the replacement of one or more atoms in the target substance by one or more foreign atoms or foreign moieties (e.g., H replaced by F; OH replaced by H; H replaced by a methyl group; H replaced by a fluoroalkyl group). Examples for a first and a second stable-labeled tracer incorporating a bioisosteric substitution may be 3-O-methyl-glucose, 2-deoxy-glucose, and 2-deoxy-2-fluoro-glucose. Thus, in the case of the bioisosteric substitution, the resulting chemical structure and elemental composition of the synthesized tracer may be similar, but not exactly the same, as that of the target substance. Therefore, the first and the at least one second stable-labeled tracers synthesized using the bioisosteric substitution approach may not exhibit the same, but only a similar behavior as the target substance. Furthermore, the general specification that the tracers are "stable-labeled" may mean that the label introduced into the tracers does not decay by a radioactive decomposition but may be stable over time. Thus, none of the stable-labeled tracers emits radiation.

In particular, the at least one second stable-labeled tracer may comprise two stable-labeled tracers such that in total (exactly or at least) three stable-labeled tracers are used in the method according to an embodiment of the present invention. All tracers may have the same or similar elemental composition as the target substance and have the same or similar chemical structure as the target substance such that all tracers biologically may behave in a manner identical or similar to the behavior of the target substance.

Ionizing the tracers and the target substance may comprise the formation of ions from the tracer and target substance molecules or derivatives thereof by various mechanisms including the addition of one or more electrons or protons to the molecules or the removal of one or more electrons or protons from the molecules. Thereby, target substance and tracer molecules or derivatives thereof are transformed into negatively or positively charged ions. In particular, negative singly-charged ions may be formed from molecules of any of the first tracer, the second tracer and the target substance if only one proton is removed from each of the molecules. Prior to the ionizing, the first tracer, the second tracer and the target substance may have been derivatized, as needed. The ions deriving from the target substance may comprise ions obtained by ionizing the target substance itself, the derivatized target substance or one of the fragments into which the target substance or derivatized target substance had been split. Similarly, the ions deriving from the first tracer may comprise ions formed by ionizing the first tracer, a derivative of the first tracer or one of the fragments into which the first tracer or the derivative of the first tracer had been split. The same holds for the ions deriving from the second tracer. Ionization of the tracers and target substances may be performed by a variety of methods, including electron ionization, chemical ionization, photo ionization, fast ion bombardment, fast atom bombardment, laser desorption, matrix-assisted laser desorption/ionization, thermospray, atmospheric pressure ion evaporation, atmospheric pressure chemical ionization and electrospray (ES) ionization. In particular, the ES ionization technique may be used to form negative singly-charged ions from the neutral tracer and target substance molecules by removing exactly one proton from each of the molecules.

After ionizing the first tracer, the second tracer and the target substance, the resulting ions are transferred to the high-resolution mass analyzer where they are separated according to their mass-to-charge (m/z) values. The first ion intensity ratio (or first relative ion intensity) may be obtained by dividing the observed intensity of the ions deriving from the first tracer by the observed intensity of the ions deriving from the target substance. The first calibration curve may have been constructed previously using a set of calibration samples with known enrichment levels of the first tracer.

When the first calibration curve is independent of enrichment levels of each of the at least one second tracer, it means that the first calibration curve does not change when at least one enrichment level of the at least one second tracer is changed. The determination of the enrichment level of the first tracer thus may not depend on any enrichment level of the at least one second tracer present in the sample. The first tracer may unambiguously be associated with a particular ion peak in a mass spectrum which may not be affected by any enrichment level of any of the at least one second tracer. In particular, the first tracer and the at least one second tracer (or in particular a combination of three stable-labeled tracers) may be selected such that to each of the tracers, a particular ion peak in the mass spectrum is associated, wherein the ion peaks do not overlap.

In conventional methods, enrichment levels of one tracer may have resulted in an ion peak which may have overlapped with another ion peak associated with another tracer.

Thus, in these conventional methods, an enrichment level of one tracer cannot be determined from one associated ion peak without taking into account enrichment levels of the other tracer whose ion peak in the mass spectrum overlaps with the ion peak of the considered tracer. Thus, in conventional methods, also a calibration curve of a particular tracer depends on enrichment levels of other tracers having overlapping ion peaks with the considered tracer.

The high-resolution mass analyzer may be operated at a mass resolving power (or mass resolution) high enough to resolve an ion peak deriving from a tracer and having a width $\Delta(m/z)$ at half maximum peak height smaller than $1\times10^{-2}$, in particular smaller than $5\times10^{-3}$ or even smaller than $3\times10^{-3}$. This mass resolving power (or mass resolution) may apply in a m/z range of 179 to 185 but which may extend even further, for example in a m/z range of 100 to 300, for example or even from 50 to 500. The required mass resolution may be achieved by various types of mass analyzers including Fourier-Transform Ion Cyclotron Resonance, Time-of-Flight, and Orbitrap mass spectrometers. The mass resolving power (or mass resolution), R, may relate to a single well resolved peak of an ion of interest and may be defined as $R=(m/z)/\Delta(m/z)$, where (m/z) is the mass-to-charge value of the ion of interest and $\Delta(m/z)$ is the width of this ion peak at half maximum peak height. By appropriately selecting the first, the second (and in particular also a third) stable-labeled tracer which are resolvable by the high-resolution mass analyzer, a simple method for determining the enrichments of the tracers may be provided, while reducing the complexity in the conversion of mass spectrometry measured ion intensity ratios to tracer enrichments and in particular also lowering the computational costs and improving the precision and accuracy of the enrichment determination. Furthermore, a greater flexibility in choosing the type and number of stable-labeled tracers that can be simultaneously employed may be provided, thereby facilitating more detailed investigations into whole-body metabolism and avoiding the use of radioactive and costly, highly-substituted stable tracers.

All stable-labeled tracers may in particular have a same nominal mass. The nominal mass may be defined as the molecular mass rounded to the accuracy of 1 Da. For example, the nominal mass of the ionized, deprotonated form of glucose is 179 Da. For example, the nominal mass of the ionized, deprotonated form of the first tracer and the second tracer of glucose may be 180 Da or 181 Da in exemplary embodiments.

According to an embodiment of the present invention, the method further comprises calculating an enrichment level of the second tracer from a second ratio of the intensity of the ions deriving from the second tracer to the intensity of the ions deriving from the target substance employing a second calibration curve being independent of the enrichment level of the first tracer.

Thus, the determination of the enrichment level of the second tracer may also be independent of the enrichment level of the first tracer and, additionally, for the (prior) construction of the second calibration curve, the knowledge of any enrichment level of the first tracer present in the calibration sample may not be required. In general, the tracers may be selected so that for the (prior) construction of a calibration curve for a particular tracer, the knowledge of any enrichment level of any other tracer present in the calibration sample may not be required, thereby also simplifying the construction of the calibration curves.

The enrichment of the first tracer and the second tracer may be determined independently of one another, since the ion peak in the mass spectrum associated with the first tracer and the ion peak associated with the second tracer can be completely distinguished from one another using the high-resolution mass analyzer. Thus, no corrections for interferences have to be applied to the ion peak intensities, thereby lowering the computational effort and improving the precision and accuracy in the determination of tracer enrichments.

According to an embodiment of the present invention, the mass resolving power (or mass resolution)—defined at 180 m/z—is equal to or greater than 75,000 when a $^{13}$C-, $^{2}$H-, and/or $^{18}$O-labeled tracer of glucose is present in the sample, and equal to or greater than 200,000 when a $^{17}$O-labeled tracer of glucose is also present in the sample. If the high-resolution mass analyzer is operated at a mass resolving power of, for instance, 180,000 at a mass-to charge (m/z) value of 180, a single peak made up of ions at 180 m/z and having a width $\Delta(m/z)$ of $1\times10^{-3}$ at half maximum peak height may be well resolved in the acquired mass spectra. The resolving power may even be higher, in particular 200,000 or between 200,000 and 250,000 when one of the first or the second tracer contains a $^{17}$O-substitution. Thereby, it may be assured that all ion peaks arising from the stable-labeled tracers within the sample may be completely distinguishable from one another.

According to an embodiment of the present invention, the method further comprises a separating or at least partly separating of undesired substances, in particular having a same elemental composition as the target substance but a different chemical structure, contained in a raw sample by performing chromatography, in particular a liquid chromatography, to obtain the sample. For example, besides glucose as the target substance, the raw sample may also contain undesired substances, like fructose and/or mannose and/or galactose, which may have same or similar elemental composition as glucose but having different chemical structure. Thus, the undesired substances may comprise one or more saccharides which would, unless being separated, interfere with the determination of the enrichments of the tracers of glucose. By separating or partly separating of undesired substances, the method may further be improved.

The chromatographic system may for example comprise an Ultra Performance Liquid Chromatography (UPLC) column and the sample may be fractionized using isocratic elution with an acetonitrile-water mixture containing ammonium hydroxide solution as an additive. The liquid chromatography system may be connected to an Orbitrap mass spectrometer through an ES ionization interface, which is in particular operating in negative ionization mode.

The ionization by ES (electrospray) may for example be performed at a source voltage of 3 to 4 kV and at a source heater temperature of 200 to 300° C., in particular around 250° C. The Orbitrap mass analyzer may for example be operated at a resolution between 20,000 and 250,000 with a scan window of m/z 100-350 and setting the automatic gain control to $10^5$ ions to enter the mass analyzer.

According to an embodiment of the present invention, a first mass value of the mass of the first tracer differs from a second mass value of the mass of the second tracer by between 1 mDa and 50 mDa, in particular between 2 mDa and 10 mDa, further in particular between 3 mDa and 6 mDa. Although the first mass and the second mass deviate only by a very small amount of for example between 3 mDa and 6 mDa, corresponding ion peaks in a mass spectrum are resolvable using the high-resolution mass spectrometry. Thus, also (combinations of) tracers, which conventionally could not be used, are now applicable, thereby offering higher flexibility in choosing the type and number of stable-labeled tracers that can be simultaneously applied. This, in turn, may facilitate more detailed investigations into whole-body metabolism and avoids the use of radioactive and/or costly, highly-substituted stable tracers.

According to an embodiment of the present invention, the first calibration curve is representable by a first mathematical function that relates (known) enrichment levels of the first tracer to values of the first ratios of ion intensities obtained by analyzing the calibration samples. Due to its independence from the enrichment levels of the second tracer, the first mathematical function may be univariate and may comprise one or more linear and/or non-linear terms with adjustable parameters. To obtain the first mathematical function, the parameters of the linear and/or nonlinear terms may be adjusted so as to closely fit the first relative ion intensity data obtained from the analysis of the calibration samples. The adjustment of the parameters may be performed using various regression methods including linear and/or non-linear least squares techniques. The obtained fit of the first mathematical function to the obtained calibration data may be depicted in a graph by using one coordinate for the enrichment values and the other for the corresponding ion intensity ratio values.

According to an embodiment of the present invention, the first calibration curve is completely independent of the enrichment level of any of the at least one second tracer, wherein the first tracer contains a $^{13}$C-substitution and the at least one second tracer contains at least one of: a $^{2}$H- and/or $^{17}$O- and/or $^{18}$O-substitution or wherein the first tracer contains a $^{2}$H-substitution and the at least one second tracer contains at least one of: a $^{13}$C- and/or $^{17}$O- and/or $^{18}$O-substitution or wherein the first tracer contains a $^{17}$O-substitution and the at least one second tracer contains at least one of: $^{13}$C- and/or $^{2}$H- and/or $^{18}$O-substitution or wherein the first tracer contains a $^{18}$O-substitution and the at least one second tracer contains at least one of: a $^{13}$C- and/or $^{2}$H- and/or $^{17}$O-substitution, wherein the first tracer and the second tracer in particular have a same nominal mass. Thus, for these combinations of the first tracer and the second tracer, the first calibration curve may be independent of the enrichment levels of the second tracer. Therefore, in the mathematical representation of the first calibration curve, enrichment levels and corresponding ion intensity ratios of the second tracer need not to be taken into account.

Completely independent may mean that due to the chosen resolution of the mass spectrometer and the chosen types of tracers, the first calibration curve and the parameters of its mathematical representation are independent of the enrichment levels of any of the at least one second tracer.

According to an embodiment of the present invention, the first calibration curve is practically independent of the enrichment of any of the at least one second tracer, wherein a nominal mass difference between the first tracer and the second tracer is at least 1 Da, wherein the first tracer contains a $^{2}$H-substitution and the at least one second tracer contains another $^{2}$H-substitution, or wherein the first tracer contains a $^{17}$O-substitution and the at least one second tracer contains another $^{17}$O-substitution, or wherein the first tracer contains a $^{18}$O-substitution and the at least one second tracer contains another $^{18}$O-substitution. Thus, for these combinations of the first tracer and the second tracer, the first calibration curve may be practically independent of the enrichment levels of the second tracer and, therefore, in its mathematical representation, enrichment levels and corresponding ion intensity ratios of the second tracer need not to be taken into account.

Practically independent may mean that due to the natural occurrence of heavier isotopes in the ions arising from the chosen second tracer, the first calibration curve may only depend on a small percentage, such as between 0 and 1% of the at least one second tracer. For example, if the first and second tracer are chosen to be a doubly and a singly $^{2}$H-labeled molecule, respectively, then the probability of the natural occurrence of an additional $^{2}$H isotope in the singly $^{2}$H-labeled second tracer may be very low (e.g., 0.1%). Thus, ions arising from this second tracer may make only a negligible contribution to the ion signal in the mass channel designated for the first tracer. Therefore, in this combination of first and second tracer, the first calibration curve and the parameters of its mathematical representation may be regarded as practically independent of the enrichment levels of the second tracer.

According to an embodiment of the present invention, the first tracer comprises a first isotopic substitution including one of a $^{2}$H-, $^{17}$O-, $^{18}$O-, $^{13}$C-substitution, wherein a first mathematical function representing the first calibration curve is obtained by the following steps, if no other tracer containing the first isotopic substitution is present in the sample, or if the nominal mass difference between tracers containing the first isotopic substitution is at least 1 Da or 2 Da, if the first isotopic substitution is a $^{13}$C-substitution: analyzing calibration samples containing known first enrichment levels of the first tracer using the high-resolution mass analyzer to obtain first calibration ratios; fitting a mathematical function to the known first enrichment levels and associated first calibration ratios, wherein the mathematical function is linear or has the following form:

$$TTR = a + b\ RI + c\ d^{RI},$$

where a, b, c, and d are fitting parameters, TTR is the tracer enrichment (expressed as tracer-to-tracee ratio), and RI is the ion intensity ratio or relative ion intensity (calculated as the intensity of ions deriving from the tracer divided by the intensity of ions deriving from the tracee, i.e. target substance).

For calibration, several calibration standards ranging for example in the tracer enrichment levels from 0 to 15% may be used. To prepare these standards, appropriate amounts of the chosen tracers may be weighed into a vial. To this an aliquot of pooled blood plasma may be added so as to obtain a plasma stock solution with a TTR value of, for example, 50%. The calibration standards covering TTR-values of for example 0 to 15% may then be prepared by making volumetric dilutions of the plasma stock solution using the pooled blood plasma. Afterwards, the calibration standards may be aliquoted into equal volumes, and three aliquots of each standard may be purified and analyzed. To calculate the amount of tracers added to the vial used for preparing the plasma stock solution, the target substance concentration in the pooled blood plasma may be measured previously. In case the target substance is glucose, glucose concentrations may be measured using a glucose oxidase-based analyzer calibrated with a particular glucose standard solution. Following the mass spectrometry analysis of the calibration standards, the obtained relative ion intensity values may then be plotted against the known tracer enrichment levels.

Generally, a linear relationship between the (known) enrichment levels and the measured relative ion intensities may be observed for the range of tracer enrichments covered by the calibration standards. However, at low enrichment levels (e.g. below 1%) of some tracers, a deviation from linearity may occur. To account for this deviation, a non-linear function may be used to fit the calibration data. The above-defined linear-exponential function, which combines a linear function with an exponential decay function, was found to be adequate to fit calibration data exhibiting non-linearity at low enrichment levels of a tracer.

To fit the linear-exponential function to calibration data of a tracer that exhibits non-linearity at low enrichment levels, the (known) enrichment values of the tracer in the calibration samples (TTR values) may be regressed on the measured relative ion intensity values (RI values) by adjusting the fitting parameters a, b, c, and d so as to minimize the sum of the weighted squared differences between the known TTR values of the tracer in the calibration samples and the calculated TTR values. This sum (S) may be expressed as:

$$S = \Sigma w_i (ttr_i - TTR_i)^2, \ i=1, \ldots, N$$

where $w_i$ is the weighting factor and the subscript i indicates the number of the calibration sample. To take the measurement uncertainties in RI into account in such a regression procedure, an inverse effective variance weighting may be applied in which the calculation of $w_i$ is based on a transformation of the experimentally determined variance in $RI_i$ ($\sigma_{RI_i}^2$) into an effective variance in $TTR_i$ ($\sigma_{EV_i}^2$). The following formula, derived by applying the rules of error propagation to the linear-exponential function, may be used to calculate $w_i$:

$$w_i = 1/\sigma_{EV_i}^2 = 1/[(b + c \, d^{RI_i} \ln(d))^2 \sigma_{RI_i}^2]$$

A non-linear least squares technique, like the Levenberg-Marquardt method, that incorporates an inverse effective variance weighting may be used to perform the described regression procedure.

Using the linear-exponential function, an adequate description of the calibration data of tracers exhibiting non-linearity at low enrichment levels was obtained and, hence, a reliable determination of the tracer enrichment levels in blood plasma samples with unknown enrichments was possible. To describe the calibration data of tracers exhibiting linearity over the entire enrichment range, a linear function (i.e., the terms containing intercept, a, and slope, b, in the linear-exponential function) may be used. Furthermore, a linear function may also be used to describe only the portion of the calibration data points which is exhibiting linearity. In this case, the calibration data points exhibiting nonlinearity may be excluded and the linear function may be fit to the remaining data points only.

According to an embodiment of the present invention, the method further comprises resolving, in a mass spectrum, a first ion peak caused by the first tracer from a second ion peak caused by the second tracer; deriving the enrichment level of the first tracer based on the first ion peak and the ion peak caused by the target substance; deriving the enrichment level of the second tracer molecule based on the second ion peak and the ion peak caused by the target substance.

The first ion peak may not overlap with the second ion peak, for example in a sense that a valley between the first peak and the second peak is less than 10% of the maximum of the first peak and the second peak.

According to an embodiment of the present invention, the target substance includes at least one further target molecule, the method comprising: ionizing a further first tracer of the further target molecule and ionizing the further target molecule of the sample; measuring intensities of ions deriving from the further target molecule and of ions deriving from the further first tracer using the high-resolution mass analyzer; calculating an enrichment level of the further first tracer from a further first ratio of the intensity of the ions deriving from the further first tracer to the intensity of the ions deriving from the further target molecule employing a further first calibration curve being independent of an enrichment level of any other tracer of the further target molecule.

The at least one further target molecule may comprise one or more further target molecules. Furthermore, at least one second further tracer may be present within the sample and enrichment levels of all tracers of the target substance as well as of all further tracers of the further target molecules may be determined using the high-resolution mass spectrometry. In particular, the first tracer, the at least one second tracer, the further first tracer and the at least one second further tracer may be selected such that their resulting ion peaks in the mass spectrum do essentially not overlap. Thereby, the enrichment level of tracers of multiple different target substances may be determined in a sample.

According to an embodiment of the present invention, the target substance and/or the further target molecule comprises or is one of: a carbohydrate, in particular a monosaccharide, a disaccharide, an oligosaccharide, a polysaccharide, in particular fructose, mannose, galactose, or starch; a carbohydrate derivative, in particular methyl glucose, deoxy glucose, deoxyfluoro glucose, or monoacetone glucose; a sugar alcohol, in particular mannitol, sorbitol, or glycerol; a ketone body, in particular betahydroxybutyrate; a lipid, in particular a fatty acid, a glycerolipid, a glycerophospholipid, a sphingolipid, a sterol lipid; an alcohol; water. Thereby, the enrichment of tracers of a great variety of target substances or further target molecules may be determined in a sample using the present invention.

According to an embodiment of the present invention, a tracer of the target substance, in particular glucose, and/or a tracer of the further target molecule is added as an internal standard to the sample and, by taking the obtained tracer enrichment level and the (known) amount of added tracer, the concentration of the target substance, in particular unlabeled glucose, and/or the concentration of the further target molecule in the sample can then be calculated. Thereby, in addition to the enrichment determination of multiple tracers of the target substance and/or the further target molecule, the concentration of the target substance and/or the further target molecule may be determined in a sample using the present invention.

According to an embodiment of the present invention, a number of ions deriving from the tracers and entering the mass analyzer is maintained below the coalescence threshold by increasing/adjusting the mass scan window to a m/z range of 179 to 186 or of 100 to 350, and/or lowering the automatic gain control to a value between $10^4$ and $10^6$ or between $10^3$ and $10^4$.

Thereby, ion clouds arising from the tracers with close m/z values may not couple (or become coalesced) when concurrently present in the high-resolution mass analyzer. In particular, it may thereby be ensured that only a defined overall number of ions in a target mass range is present inside the mass analyzer at a given time, wherein this overall number of ions is selected such that the specific number of ions in the clouds deriving from tracers with close m/z values is maintained below their coalescence threshold. The overall number of ions entering the mass analyzer may be controlled by adjusting the mass scan window and/or automatic gain control of the mass analyzer. For example, to avoid coalescence, the width of the mass scan window may be increased and/or the automatic gain control may be set to lower values. Coalescence of ion clouds would result in the generation of a single ion peak instead of multiple peaks.

Thus, the high-resolution properties of the mass analyzer may be lost when coalescence occurs.

According to an embodiment of the present invention, an intensity of the ion peak deriving from the target substance is maintained above a threshold level of $1.0 \times 10^7$ or of $1.0 \times 10^8$ arbitrary units by increasing the amount of sample injected into the chromatograph to a value between 1 and 3 µl or between 3 and 10 µl, and/or decreasing the mass scan window to a m/z range of 100 to 350 or of 179 to 186, and/or increasing the automatic gain control to a value between $10^3$ and $10^4$ or between $10^4$ and $10^6$.

Thereby, a high accuracy in the measurement of the relative ion intensity for a tracer of the target substance may be achieved. Otherwise, erratic measurements of the relative ion intensity for tracers of the target substance may be obtained when the intensity of the ion peak deriving from the target substance falls below a certain threshold level. This threshold level may lie at around $1.0 \times 10^7$, when peak heights are considered or at around $1.0 \times 10^8$ arbitrary units, when integrated ion peak intensities are considered. In particular, the lower an integrated ion peak intensity of a target substance falls below the threshold level, the higher the errors in the relative ion intensity measurements may be. However, a high accuracy in the measurement of the relative ion intensity for a tracer may be obtained as soon as intensities of the ion peak deriving from the target substance are higher than the threshold value. The intensity of the ion peak deriving from the target substance may be controlled by adjusting the mass scan window width and/or the automatic gain control and/or the amount of sample injected into the chromatograph. For example, to increase the intensity of the ion peak associated with the target substance, the amount of sample injected into the chromatograph may be increased and/or the width of the mass scan window may be decreased and/or the automatic gain control may be set to higher values. In addition, the intensity of the ion peak associated with the target substance may also be controlled by adjusting the amount of sample used in a possible sample purification step. For example, to increase the intensity of the ion peak, the amount of sample taken in a sample purification process may be increased to a value between 5 and 300 µl or between 300 and 500 µl.

It should be understood that features, individually or in any combination, disclosed, described or explained for a method for determining enrichment levels of multiple tracers may also be applicable to a set of tracer molecules for determining metabolism of a target substance and may also be applicable to a system for determining metabolism of a target substance according to embodiments of the present invention and vice versa.

According to an embodiment of the present invention it is provided a set of molecules for determining metabolism of a target substance by high-resolution mass spectroscopy, the set comprising: at least a first and a second tracer each administrable to a living organism, each having a chemical structure and an elemental composition of the target substance and having the same nominal mass, wherein the first and the second tracer being selected such as to be resolvable using high-resolution mass spectroscopy and their enrichment being quantifiable in a sample extracted from the living organism, in particular from a body fluid of the living organism.

Metabolism of a target substance may comprise anabolism, catabolism, production, utilization, uptake, disposal, excretion, appearance, disappearance, clearance, transportation, diffusion, convection internalization, fragmentation and/or derivatization of the target substance.

The first and second tracer may be selected to be usable and to be used within a method for determining the enrichment levels of the tracers according to an embodiment of the present invention. In particular, the set may further comprise at least one third tracer which may also be selected to be usable and to be used within a method for determining the enrichment levels of the tracers. All tracers of the set may have the same nominal mass. Thereby, costs of the tracers may be reduced. In particular, the tracers may each contain only one isotopic substitution. Thereby, the need of using costly, multiply-substituted tracers may be eliminated. The set represents a particular selected set of molecules such that when introduced in a high-resolution mass spectrometer, the corresponding ion peaks are resolvable from each other. Conventionally, a set of molecules for determining metabolism of a target substance may have comprised tracers having different nominal mass. All tracers within the set may be used in a method for determining the respective enrichment levels of all tracers according to an above-described embodiment of the present invention.

According to an embodiment of the present invention it is provided a system for determining metabolism of a target substance by high-resolution mass spectroscopy, the system comprising: a set of at least two tracers according to the preceding descriptions; and a high-resolution mass spectroscopy apparatus configured to resolve from each other the at least two tracers, the system in particular further comprising: a chromatograph adapted to partly separate constituents of the sample into fractions of constituents that are suppliable to the high-resolution mass spectroscopy apparatus.

DETAILED DESCRIPTION OF ILLUSTRATED EMBODIMENTS

Figure 1:
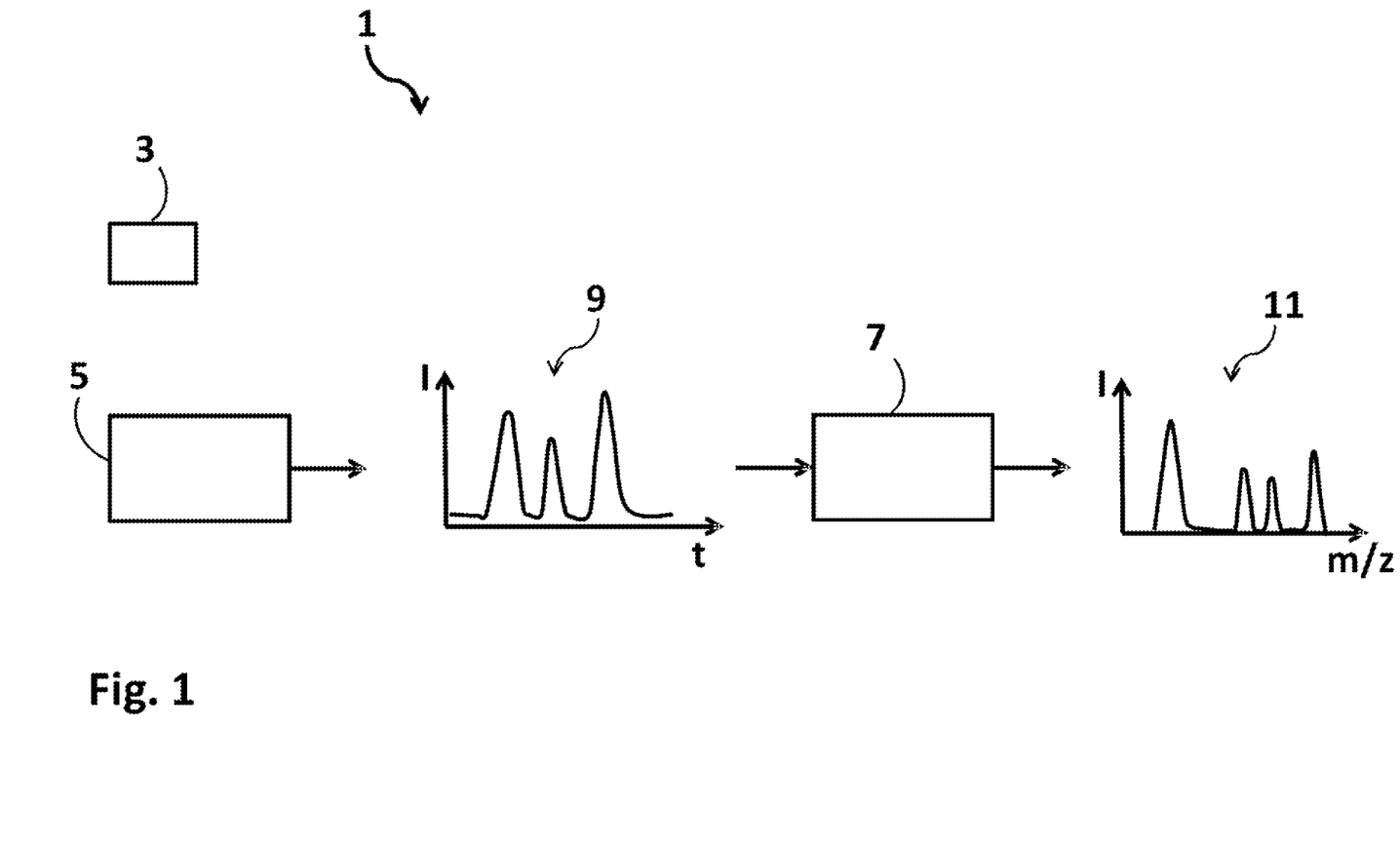
FIG. 1 schematically illustrates a system for determining metabolism of a target substance according to an embodiment of the present invention.

The system 1 for determining metabolism of a target substance, in particular glucose, illustrated schematically in FIG. 1, comprises a set, according to an embodiment of the present invention, of at least two tracers of the target substance which are contained in a sample 3. Further, the system 1 comprises a liquid chromatograph 5 to which the sample 3 is applied. The system 1 further comprises a high-resolution mass spectrometry apparatus 7 to which one or more fractions as derived using the chromatograph 5 are supplied or loaded.

The liquid chromatograph 5 comprises an ultra-performance liquid chromatography BEH amide column (UPLC BEH amide column) equipped with a column in-line filter. For determination of the enrichment of tracers of glucose (an exemplary target substance), a sample volume of 4 µl from the sample 3 is injected and isocratic elution is performed with acetonitrile/$H_2O$ (8:2; v/v) containing 0.1 vol.-% of ammonium hydroxide solution as additive at a flow rate of 150 μL/min for 15 minutes.

The mass spectrometry apparatus 7 is an Orbitrap mass spectrometer that is connected to the liquid chromatograph 5 through a heated-electrospray ionization interface. For determination of the enrichment of tracers of the exemplary target substance (i.e., glucose), the heated-electrospray ionization interface is operated in the negative ionization mode using the following electrospray parameters: source voltage, 3.8 kV; a source heater temperature, 250° C.; sheath, auxiliary and sweep gas, 30, 12 and 1 arbitrary units, respectively; capillary temperature, 300° C. Thereby, the Orbitrap mass analyzer 7 is operated in full scan mode at a target resolution of 100,000 with a scan window of m/z 100-350. Automatic gain control is set to allow $10^5$ ions to enter the mass analyzer. Using the water loss of monoisotopic glucose (m/z 161.0455) as lock mass, deprotonated ions of glucose and sorbitol/mannitol are then monitored at mass-to-charge values as given in Table 1 below. The integration of the observed ion peaks is performed using a software tool.

mass spectrometry apparatus 7 alone. As can be appreciated from the liquid chromatography elution profile 9 illustrated in FIG. 2, fructose and mannose are completely resolved from glucose, but glucose and galactose are only partially resolved on the column. However, since galactose may most often be present in negligible concentrations in the sample 3, the determination of glucose tracer enrichments may not be affected by an incomplete separation of glucose and galactose.

Figure 2:
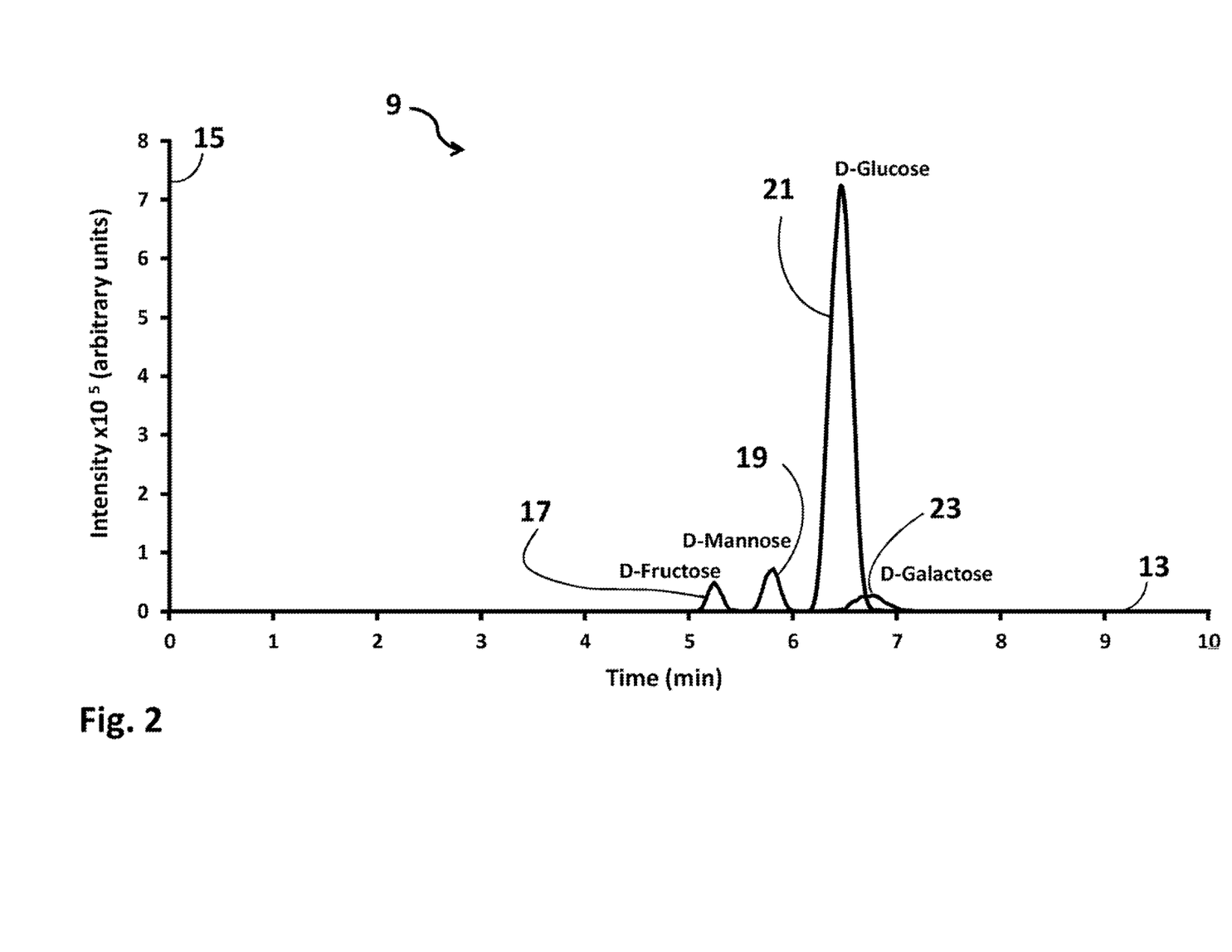
FIG. 2 illustrates an example of an elution profile of a liquid chromatograph used in embodiments of the present invention.

Thus, fractions containing the peak 21 are then loaded into the mass spectrometry apparatus 7 to determine levels of at least a first and a second tracer contained within the sample 3. Besides the naturally occurring isotopologues of glucose (i.e., isotopologues of the exemplary target substance), the sample 3 may also contain tracers of glucose, for example, those listed in Table 1, in particular combinations thereof. Since the chemical properties of the listed tracers are the same as those of the isotopologues of glucose, the tracers are also comprised in the peak 21. Fractions containing the peak 21 are then transferred to the mass spectrometry apparatus 7 to determine enrichments of at least a first and a second tracer contained within the sample 3.

TABLE 1

Tracers of Glucose as well as Natural Abundance & Exact Mass of Stable Isotopologues of Glucose

| Tracers of Glucose | | Isotopologues of | Natural Abundance | Nominal Mass | Exact Mass (Da) | | Mass Difference |
|---|---|---|---|---|---|---|---|
| No. | Type | Glucose[a] | (%)[b] | (Da) | M | [M − H]⁻ | (mDa)[c] |
| | | $^{12}C_6{}^1H_{12}{}^{16}O_6$ | 100.00000 | 180 | 180.06339 | 179.05611 | |
| 1 | [1-$^{13}C_1$]glucose | $\underline{^{13}C_1{}^{12}C_5{}^1H_{12}{}^{16}O_6}$ | 6.48944 | 181 | 181.06674 | 180.05947 | 2.922 |
| | | $^{12}C_6{}^1H_{12}{}^{17}O_1{}^{16}O_5$ | 0.22856 | 181 | 181.06761 | 180.06033 | 2.060 |
| 2 | [1-$^2H_1$]glucose | $\underline{^{12}C_6{}^2H_1{}^1H_{11}{}^{16}O_6}$ | 0.13802 | 181 | 181.06966 | 180.06239 | 0.000 |
| | | $^{12}C_6{}^1H_{12}{}^{18}O_1{}^{16}O_5$ | 1.23300 | 182 | 182.06763 | 181.06036 | 8.308 |
| 3 | [1,6-$^{13}C_2$]glucose | $\underline{^{13}C_2{}^{12}C_4{}^1H_{12}{}^{16}O_6}$ | 0.17547 | 182 | 182.07010 | 181.06282 | 5.844 |
| | | $^{13}C_1{}^{12}C_5{}^1H_{12}{}^{17}O_1{}^{16}O_5$ | 0.01483 | 182 | 182.07096 | 181.06368 | 4.982 |
| | | $^{12}C_6{}^1H_{12}{}^{17}O_2{}^{16}O_4$ | 0.00022 | 182 | 182.07182 | 181.06455 | 4.119 |
| | | $^{13}C_1{}^{12}C_5{}^2H_1{}^1H_{11}{}^{16}O_6$ | 0.00896 | 182 | 182.07302 | 181.06574 | 2.922 |
| | | $^{12}C_6{}^2H_1{}^1H_{11}{}^{17}O_1{}^{16}O_5$ | 0.00032 | 182 | 182.07388 | 181.06661 | 2.060 |
| 4 | [6,6-$^2H_2$]glucose | $\underline{^{12}C_6{}^2H_2{}^1H_{10}{}^{16}O_6}$ | 0.00009 | 182 | 182.07594 | 181.06867 | 0.000 |
| | | $^{12}C_6{}^1H_{14}{}^{16}O_6{}^d$ | n.a. | | 182.07904 | 181.07176 | 3.097 |
| 5 | [U-$^{13}C_6$]glucose | $\underline{^{13}C_6{}^1H_{12}{}^{16}O_6}$ | <0.00001 | 186 | 186.08352 | 185.07624 | |

[a]Isotopologues used as tracers are underlined.
[b]Relative to monoisotopic glucose.
[c]Difference to the ion mass of [$^{12}C_6{}^2H_1{}^1H_{11}{}^{16}O_6$] or [$^{12}C_6{}^2H_1{}^1H_{10}{}^{16}O_6$].
[d] Monoisotropic sorbitol and mannitol Application of the sample 3 containing the at least two tracers of the target substance results in an elution profile 9 from which individual fractions may be transferred to the mass spectrometry apparatus 7. For one or more fractions eluting from the chromatograph 5, the high-resolution mass spectrometry apparatus 7 determines a mass spectrum 11 wherein the ionized constituents of the respective fraction are separated according to their mass-to-charge values.

FIG. 2 illustrates an example of elution profile 9 as obtained after injecting 5 μg/ml of glucose, mannose, and galactose as well as 100 μg/ml of glucose into the chromatograph 5. Thereby, the abscissa 13 denotes the time in minutes, while the ordinate 15 denotes the intensity of the fractions eluting from the column contained in the chromatograph 5. The elution profile 9 comprises a number of peaks 17, 19, 21 and 23. In particular, the peak 17 corresponds to fructose, the peak 19 corresponds to mannose, the peak 21 corresponds to glucose and the peak 23 corresponds to galactose. Fructose, mannose, and galactose have the same elemental composition and mass as glucose (hexoses) and, therefore, cannot be separated from each other using the The tracers listed in Table 1 and labeled as tracer number 1 to tracer number 5 may be present in the sample in particular combinations thereof. As can be seen, these tracers contain at least one $^{13}C$-, or $^2H$-substitution in specific carbon positions. Tracer 1 contains one $^{13}C$-substitution in the first carbon position, whereas tracer 2 contains exactly one $^2H$-substitution in the first carbon position. Furthermore, tracer 3 contains two $^{13}C$-substitutions, one in the first and one in the sixth carbon position, and tracer 4 contains two $^2H$-substitutions, both in the sixth carbon position. Finally, tracer 5 contains $^{13}C$-substitutions in all six carbon positions of the tracer molecule.

As can be taken from Table 1, the most abundant naturally occurring isotopologue of (unlabeled) glucose has a nominal mass of 180 Da. Most abundant isotopologues of the tracer 1 and 2 have a nominal mass of 181 Da, the most abundant isotopologues of the tracer 3 and 4 have a nominal mass of 182 Da and the most abundant isotopologue of tracer 5 has a nominal mass of 186 Da. Although the isotopologues of tracer 1 and 2 have the same nominal mass, they may be resolved using the high-resolution mass spectrometry apparatus 7. The same holds for the isotopologues of tracer 3 and 4.

Figure 3A:
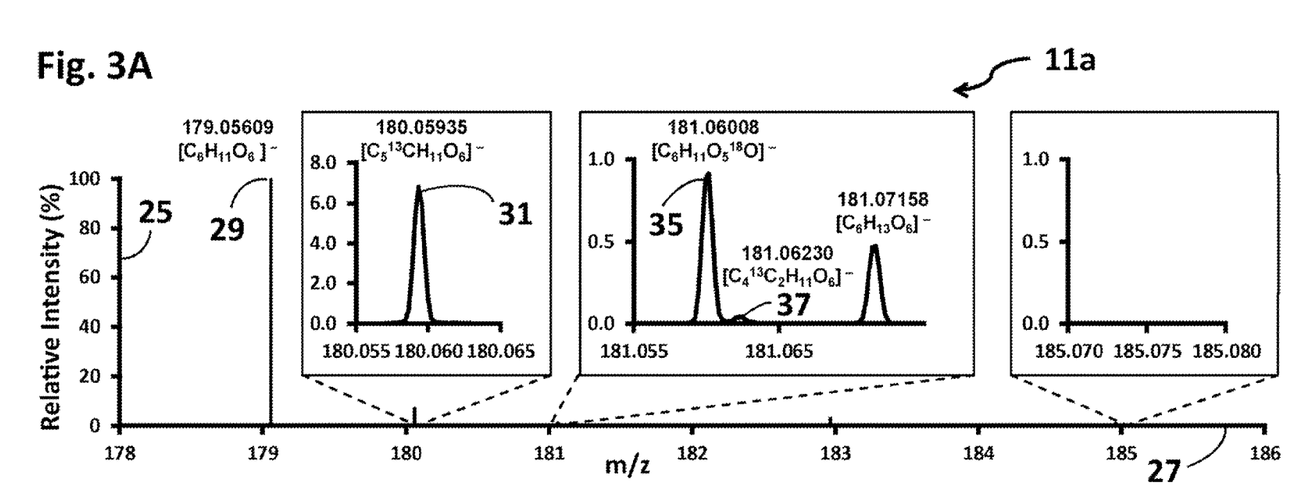
FIGS. 3A and 3B illustrate exemplary mass spectra considered in embodiments of the present invention.
Figure 3B:
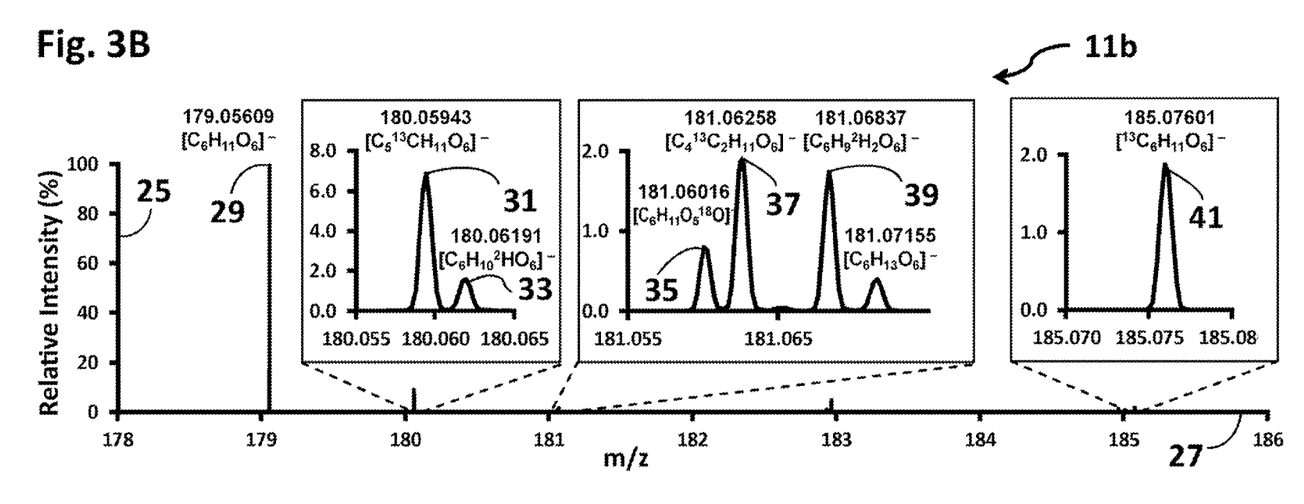

FIGS. 3A and 3B show high-resolution negative-ion mass spectra 11a and 11b acquired using the Orbitrap Velos mass analyzer 7 illustrated in FIG. 1. Thereby, the ordinates 25 indicate the relative ion intensity, while the abscissas 27 indicate the mass-to-charge (m/z) values.

The mass spectrum 11a, illustrated in FIG. 3A, was recorded from a blank human blood plasma sample containing naturally abundant levels of glucose isotopologues, while the mass spectrum 11b, shown in FIG. 3B, was recorded from a human blood sample that contained the tracer 2, 3, 4 and 5 at enrichment levels of 2%. Insets in FIGS. 3A and 3B show magnified views of the m/z-ranges containing the ion peaks arising from the isotopologues of natural glucose and of tracers 2, 3, 4 and 5. Also shown are the isotopic composition and the exact m/z-value of the individual ion peaks arising from the isotopologues of the natural glucose and the tracers. The mass spectra 11a and 11b were acquired with a resolution or resolving power exceeding 175,000 (defined at m/z 180).

The ion peak 29 in FIGS. 3A and 3B arises from the most abundant naturally occurring isotopologue of glucose. Furthermore, ion peak 31, which has a relative intensity of about 6.45%, arises from the $^{13}C$-containing, second most abundant naturally occurring isotopologue of glucose (i.e., $^{13}C_1{}^{12}C_5{}^1H_{12}{}^{16}O_6$). Since tracer 1 contains one $^{13}C$-substitution (i.e., [1-$^{13}C$]glucose), ions arising from the most abundant isotopologue of tracer 1 will have exactly the same m/z value as the ions of peak 31 and, hence, will contribute to this ion peak. The ion peak 33 in the mass spectrum 11b arises from the most abundant isotopologue of the singly $^2H$-labeled tracer 2. As can be seen, ions of this peak and ions of peak 31, which may arise from the singly $^{13}C$-labeled tracer 1 and the second most abundant naturally occurring isotopologue of glucose, can be distinguished from each other. Importantly this distinction can be achieved despite the very small mass difference between the ions of peak 31 and 33 (i.e., 2.922 mDa, see Table 1). Thus, enrichments of the singly $^{13}C$-labeled tracer 1 and the singly $^2H$-labeled tracer 2 can be determined independently of one another, since the ion peaks associated with these tracers (i.e., peaks 31 and 33) can be completely distinguished from one another using the high-resolution mass analyzer 7. Furthermore, ion peak 35 in mass spectra 11a, 11b arises from the $^{18}O$-containing, third most abundant naturally occurring isotopologue (i.e., $^{12}C_6{}^1H_{12}{}^{18}O_1{}^{16}O_5$ with a natural abundance of 1.23%). Ion peak 37 arises from the most abundant isotopologue of the doubly $^{13}C$-labeled tracer 3 and from the $^{13}C$-containing, less abundant naturally occurring isotopologue of glucose (i.e., $^{13}C_2{}^{12}C_5{}^1H_{12}{}^{16}O_6$ with a natural abundance of 0.18%). Ion peak 39 in the mass spectrum 11b arises from the most abundant isotopologue of the doubly $^2H$-labeled tracer 4. Again, ions of this peak and ions of peak 37 can be distinguished from each other, despite the very small mass difference between them (i.e., 5.8 mDa, see Table 1). Therefore, enrichments of the doubly $^{13}C$-labeled tracer 3 and the doubly $^2H$-labeled tracer 4 can also be determined independently of one another, since the ion peaks associated with these tracers (i.e., peaks 37 and 39) can be completely distinguished from one another using the high-resolution mass spectrometry apparatus 7, Finally, the ion peak 41 in mass spectrum 11b arises from the most abundant isotopologue of tracer 5 incorporating six $^{13}C$-substitutions.

In the sample, different tracer combinations according to embodiments of the present invention may be present. For example, tracer 2, 4, and 5 may be concurrently present in the sample. For this combination, termed triple-tracer combination 1, calibration curves are illustrated in FIGS. 4A, 4B and 4C. Furthermore, calibration curves for another tracer combination, termed triple-tracer combination 2 and comprising tracer, 2, 4 and 3, are illustrated in FIGS. 5A, 5B and 5C. Moreover, calibration curves for a third tracer combination, termed triple-tracer combination 3 and comprising tracer 1, 4, and 5, are illustrated in FIGS. 6A, 6B and 6C.

In FIGS. 4A, 4B, 4C, 5A, 5B, 5C and 6A, 6B, 6C, abscissas 43 denote the relative ion intensity (RI) or ion intensity ratio (calculated as the intensity of ions deriving from the respective tracer divided by the intensity of ions deriving from the tracee, i.e., unlabeled glucose), while ordinates 45 denote the tracer enrichment (expressed as the tracer-to-tracee ratio TTR). Furthermore, the circles, diamonds and triangles shown in the panels of FIGS. 4 to 6 denote the experimental data points obtained from the analysis of the calibration samples. In addition, also shown are fitting parameters of the mathematical representation of the calibration curves, insets with enlarged views of curve fits in the enrichment range from 0 to 2%, and the uncertainty in the TTR-determination (expressed as the one-sided lower and upper 95%-confidence intervals; 95%-CI) for the case that for a sample with unknown enrichments, the mean of the results of duplicative relative ion intensity measurements is used.

FIGS. 4A, 4B and 4C illustrate the calibration curves 47, 49, 51 obtained for the tracer 2, 4, and 5, respectively. Furthermore, FIGS. 5A, 5B and 5C depict the calibration curves 53, 55, 57 obtained from the tracer 2, 4, and 3, respectively, and FIGS. 6A, 6B and 6C depict the calibration curves 59, 61 and 63 obtained for the tracer 1, 4 and 5, respectively.

Figure 4:
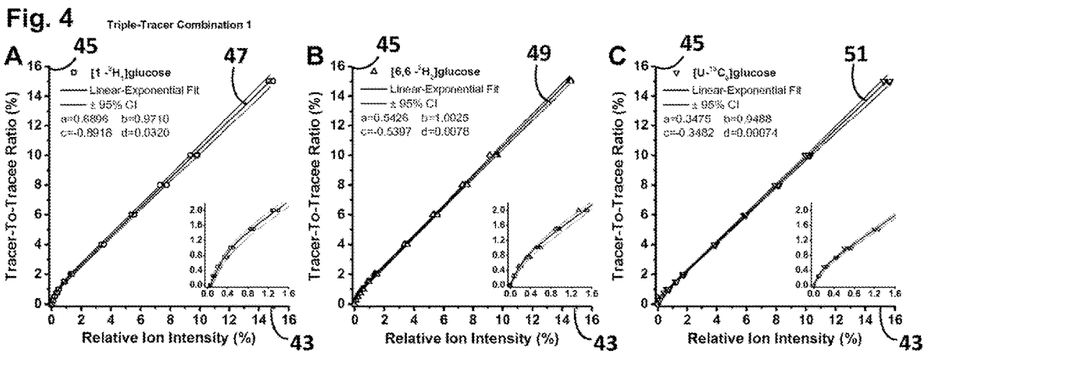
FIGS. 4A, 4B, 4C, 5A, 5B, 5C and 6A, 6B, and 6C illustrate examples of calibration curves as used in embodiments according to the present invention.
Figure 5:
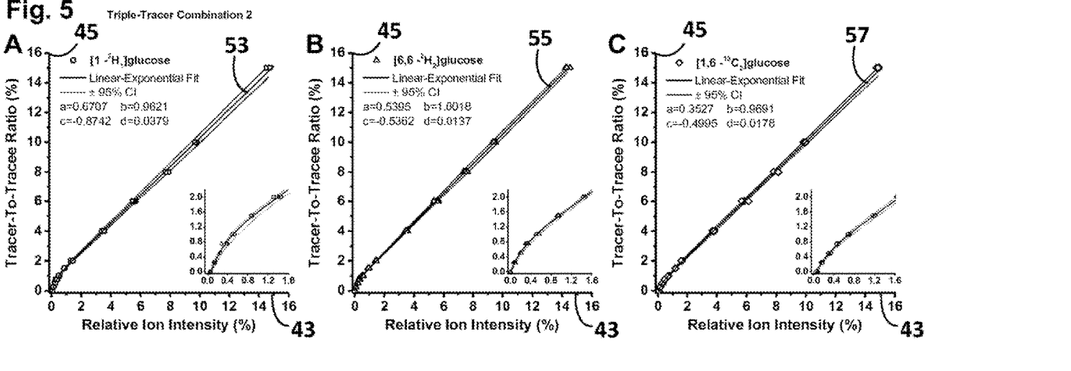
Figure 6:
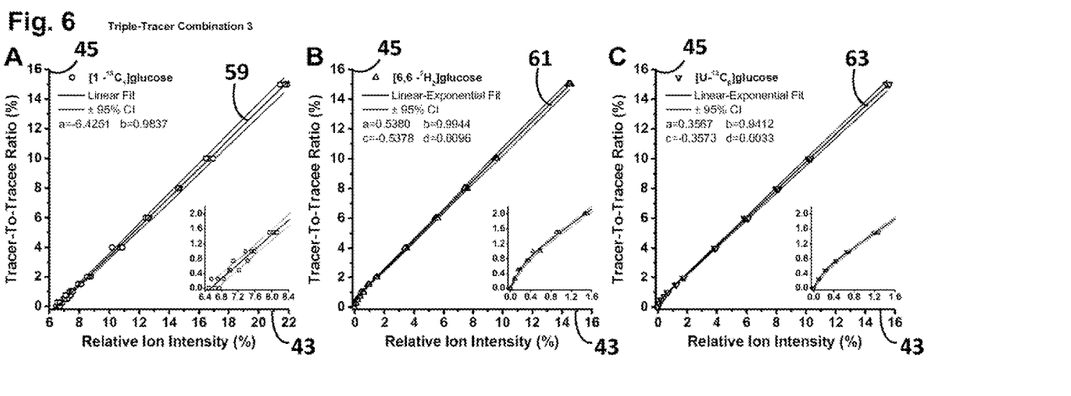

It can be well appreciated from the calibration data points (i.e., circles, triangles, and diamonds) plotted in FIGS. 4 to 6 that in all cases a linear relationship between TTR and RI values exists for TTR values larger than ~1%. However, in the TTR range between 0 and ~1%, deviations from linearity occur in all but one of the plots, the exception being the plot for tracer 1 (i.e., [1-$^{13}C_1$]glucose in FIG. 6A). Therefore, to obtain the calibration curve 47, 49, 51, 53, 55, 57, 61 and 63, the above-defined linear-exponential function (i.e., TTR=a+b RI+c d RI) was fit to the calibration data for the respective tracer 2, 4, 5, 2, 4, 3, 4, and 5, whereas to obtain calibration curve 59, the parameter values of the exponential component of the linear exponential function were set to 0 and only its linear component was fit to the calibration data for tracer 1. The calibration curve 47, 49, 51, 53, 55, 57, 59, 61 and 63 are, thus, represented by the above-defined linear-exponential function together with the obtained fitting parameter values given in the panels of FIGS. 4 to 6.

The calibration data illustrated in FIGS. 4 to 6 were obtained by analyzing a set of 12 standards ranging in the TTR values from 0 to 15% (i.e., 0, 0.25, 0.5, 0.75, 1, 1.5, 2, 4, 6, 8, 10, 15%). This set of calibration standards was prepared for each of the three triple-tracer combinations as described above. To calculate the RI values (i.e., the relative intensity values), the ion peak intensity arising from the tracer (e.g., intensity of the peak 33 for the tracer 2 in FIG. 3B) is divided by the ion peak intensity arising from the tracee (e.g., the intensity of the peak 29 in FIG. 3A or FIG. 3B). To fit the linear-exponential function to the calibration data and to get the numerical values of the (unknown) fitting parameters, a nonlinear least-squares technique (i.e. Levenberg-Marquadt method), that incorporated the above-described inverse effective variance weighting, was applied. However, to perform the inverse effective variance weighting, the uncertainty in the RI measurement (expressed as variance, $\sigma_{RI}{}^2$, or coefficient of variation, CV) has to be known. Therefore, prior to the curve fitting, the uncertainty in the RI measurement was experimentally determined by analyzing replicates of human plasma samples enriched with known amounts of the tracers. To prepare the replicates, a series of 13 human plasma samples ranging in the TTR values from 0 to 15% (i.e., 0, 0.1, 0.2, 0.3, 0.4, 0.5, 1, 2, 4, 6, 8, 10, 15%) was first produced for each triple-tracer combination as described above for calibration standards. Afterwards, each plasma sample was aliquoted, and 10 aliquots of each sample were purified and analyzed. Measures of uncertainty ($\sigma_{RI}^2$, CV) were then calculated from the obtained RI values. Results of this uncertainty evaluation for the individual tracers are shown in Table 2.

TABLE 2

Uncertainty Values Obtained for Relative Ion Intensity Measurements
CV for Measuring Relative Ion Intensity (%)[a,b]

| TTR-Level (%) | [1-$^2$H$_1$] glucose | [6,6-$^2$H$_2$] glucose | [1-$^{13}$C$_1$] glucose | [1,6-$^{13}$C$_2$] glucose | [U-$^{13}$C$_6$] glucose |
|---|---|---|---|---|---|
| 15 | 2.1 | 1.5 | 1.9 | 1.5 | 2.1 |
| 10 | 2.7 | 2.1 | 1.8 | 1.4 | 1.7 |
| 8 | 2.3 | 1.9 | 2.1 | 1.4 | 1.8 |
| 6 | 2.5 | 1.6 | 2.1 | 1.7 | 1.9 |
| 4 | 3.8 | 2.9 | 1.2 | 3.4 | 2.0 |
| 2 | 5.4 | 4.1 | 1.7 | 3.3 | 2.9 |
| 1 | 12.1 | 8.1 | 1.3 | 7.5 | 5.9 |
| 0.5 | 12.3 | 9.8 | 1.8 | 3.0 | 10.6 |
| 0.4 | 11.5 | 11.0 | 1.7 | 7.5 | 13.6 |
| 0.3 | 25.1 | 10.8 | 2.0 | 7.1 | 10.9 |
| 0.2 | 23.1 | 19.6 | 2.1 | 8.0 | 30.3 |
| 0.1 | 34.7 | 34.9 | 2.1 | 18.2 | 35.0 |
| 0 | 33.1 | N/D | 1.8 | 14.7 | N/D |

[a]CV . . . coefficient of variation defined as: standard deviation/mean × 100;
[b]N/D . . . not defined (CV is not defined if sample mean is zero);

To assess the uncertainty associated with the determination of the fitting parameters, a Monte Carlo simulation was performed. In this simulation, 5000 synthetic data sets were generated for each calibration data set by randomly drawing new RI values from Gaussian distributions with the experimentally determined standard deviations (i.e., $\sigma_{RI}^2$ values obtained for the 12 enrichment levels of a set) and locations (i.e., means of the triplicate RI values observed at the 12 enrichment levels of a set). Each synthetic data set was then fit with the linear-exponential function, and the 5000 values thus obtained for each fitting parameter were used to calculate measures of location (mean$_{MC}$) and uncertainty (SD$_{MC}$). Results of the assessment of the uncertainty associated with the determination of the fitting parameters are shown in Table 3.

TABLE 3

Parameter Results Obtained From Fitting the Linear-Exponential Function to Calibration Data Sets

| Glucose Tracer | Triple Combination (TC) | Linear-Exponential Function Parameters (mean$_{MC}$, SD$_{MC}$)[a,b] | | | |
|---|---|---|---|---|---|
| | | a | b | c | d |
| [1-$^2$H$_1$]glucose | TC 1 | 0.702 (0.064) | 0.969 (0.010) | −0.872 (0.068) | 0.04656 (0.05307) |
| | TC 2 | 0.695 (0.038) | 0.959 (0.009) | −0.842 (0.069) | 0.05928 (0.02954) |
| [6,6-$^2$H$_2$]glucose | TC 1 | 0.545 (0.038) | 1.002 (0.007) | −0.548 (0.038) | 0.01062 (0.00755) |
| | TC 2 | 0.540 (0.020) | 1.001 (0.005) | −0.545 (0.020) | 0.01426 (0.00599) |
| | TC 3 | 0.541 (0.025) | 0.993 (0.007) | −0.545 (0.025) | 0.01244 (0.00643) |
| [1-$^{13}$C$_1$]glucose | TC 3 | −6.428 (0.083) | 0.984 (0.010) | | |
| [1,6-$^{13}$C$_2$]glucose | TC 2 | 0.358 (0.024) | 0.968 (0.006) | −0.515 (0.027) | 0.01952 (0.00872) |
| [U-$^{13}$C$_6$]glucose | TC 1 | 0.344 (0.017) | 0.949 (0.005) | −0.350 (0.017) | 0.00099 (0.00125) |
| | TC 2 | 0.358 (0.016) | 0.941 (0.006) | −0.365 (0.017) | 0.00416 (0.00344) |

Figure 7:
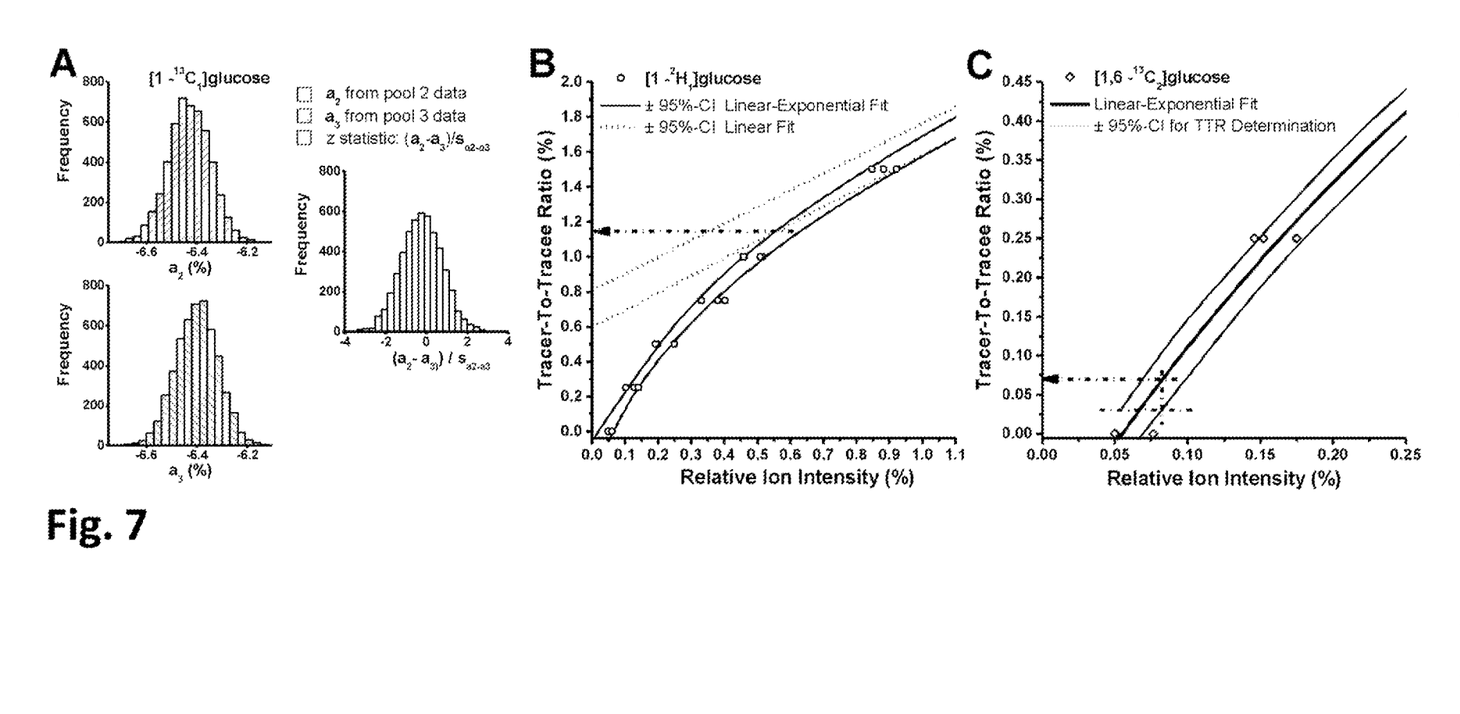
FIGS. 7A, 7B and 7C illustrate examples of statistical procedures for validation of the method considered in embodiments of the present invention.

[a]Shown are means and standard deviations of the parameter's frequency distributions obtained by applying the Monte Carlo method;
[b]No significant differences were found between parameter values obtained for calibration sets with low tracee concentration (i.e., sets prepared from plasma pool 2; upper part) and those obtained for calibration sets with high tracee concentration (i.e., sets prepared from plasma pool 3; bottom part);

FIGS. 7A, 7B and 7C illustrate further statistical procedures for the validation of the method considered in embodiments of the present invention. To compare the fitting parameter values obtained for the individual calibration sets with one another (e.g., parameters obtained for triple-tracer combination 1 with those obtained for triple-tracer combination 2), the z statistic ($z=\delta/\sigma_\delta$) was used in which the mean of the difference between the parameters obtained for the combination 1 and 2, $\delta$, as well as the standard deviation of this difference, $\sigma_\delta$, were calculated from the Monte Carlo simulation results. Any z value whose absolute value was less than 1.96 resulted in the acceptance of the null hypothesis that $\delta=0$. A representative example of the comparison of fitting parameters using the z statistic is shown in FIG. 7A.

To assess the linear ranges of the method, one-sided lower and upper 95%-CI for linear-exponential function fits were calculated for each tracer by determining the 5 and 95 percentile values from the frequency distribution of the 5000 calibration curve fits obtained for each tracer in a triple combination. These 95%-CI values were compared to those derived from the frequency distribution of curve fits obtained by using the linear part of the linear-exponential function only (i.e., terms containing parameter a and b). The lower bound of the linear range of the enrichment determination was then determined for each tracer as the point where the lower 95%-prediction band obtained for the linear curve fits crosses the upper 95%-prediction band obtained for the linear-exponential curve fits. A representative example of the determination of the linear range is shown in FIG. 7B. Results of the assessment of the linear ranges of the calibration curves for the individual tracers are shown in Table 4.

TABLE 4

Limits of Detection and Linear Ranges

| Glucose Tracer | Limit of Detection (%) | Lower Bound of Linear Range (%) |
|---|---|---|
| [1-$^2$H$_1$]glucose | 0.200 | 1.26 |

TABLE 4-continued

Limits of Detection and Linear Ranges

| Glucose Tracer | Limit of Detection (%) | Lower Bound of Linear Range (%) |
|---|---|---|
| [6,6-$^2$H$_2$]glucose | 0.037 | 0.99 |
| [1-$^{13}$C$_1$]glucose | 0.310 | 0.00 |
| [1,6-$^{13}$C$_2$]glucose | 0.071 | 0.87 |
| [U-$^{13}$C$_6$]glucose | 0.040 | 0.63 |

To assess the uncertainty associated with the TTR determination when it is based on the use of the mean of the results of duplicate RI measurements, a second Monte Carlo simulation was performed in which 1000 new RI values were generated for enrichment levels of 0, 0.1, 0.2, 0.25, 0.3, 0.4, 0.5, 0.75, 1.0, 1.5, 2, 4, 6, 8, 10, and 15% by drawing random samples from Gaussian distributions centered at locations equal to the means of the observed RI values and with standard deviations equal to the obtained $\sigma_{RI}$ values divided by $\sqrt{2}$. Following this, for a given calibration set, the obtained RI values and the corresponding 5000 calibration curve fits generated as described above were used to calculate $5 \times 10^6$ TTR values for each enrichment level. The CV and the one-sided lower and upper 95%-CI for the TTR determination were then calculated from the frequency distribution of the $5 \times 10^6$ TTR values obtained for each enrichment level. Results of the assessment of the uncertainty associated with the TTR determination for the individual tracers are shown in Table 5 and in FIGS. 4 to 6.

TABLE 5

Uncertainty Values Obtained for Determination of Tracer Enrichments
CV for Determining Tracer Enrichment (%)$^{a,b,c,d}$

| TTR-Level (%) | [1-$^2$H$_1$] glucose | [6,6-$^2$H$_2$] glucose | [1-$^{13}$C$_1$] glucose | [1,6-$^{13}$C$_2$] glucose | [U-$^{13}$C$_6$] glucose |
|---|---|---|---|---|---|
| 15 | 1.6 | 1.1 | 2.1 | 1.1 | 1.5 |
| 10 | 2.0 | 1.4 | 2.2 | 1.1 | 1.2 |
| 8 | 1.6 | 1.3 | 2.7 | 1.0 | 1.3 |
| 6 | 1.7 | 1.0 | 3.0 | 1.3 | 1.3 |
| 4 | 2.3 | 1.8 | 2.3 | 2.2 | 1.4 |
| 2 | 3.0 | 2.3 | 5.0 | 2.2 | 1.8 |
| 1 | 6.8 | 3.7 | 7.8 | 4.2 | 3.2 |
| 0.5 | 9.9 | 6.1 | 17.1 | 2.4 | 5.8 |
| 0.4 | 10.6 | 7.3 | 22.5 | 5.8 | 8.2 |
| 0.3 | 24.7 | 7.8 | <u>32.4</u> | 6.4 | 8.1 |
| 0.2 | <u>29.8</u> | 13.5 | 50.1 | 9.4 | 20.2 |
| 0.1 | 71.4 | <u>25.4</u> | 93.4 | <u>30.3</u> | <u>25.4</u> |
| 0 | N/D | N/D | N/D | N/D | N/D |

$^a$CV . . . coefficient of variation defined as: standard deviation/mean × 100;
$^b$N/D . . . not defined (CV is not defined if sample mean is zero);
$^c$Calculated for the case when the mean of duplicate RI measurements are used for the TTR determination;
$^d$CVs for enrichment levels that are equal or close to the LOD levels are underlined;

From the obtained 95%-CI values, the lower limits of detection (LOD) were calculated for each tracer by employing the procedure graphically illustrated in FIG. 7C. It involves the drawing of a horizontal line from the lower end of the upper 95%-prediction band to the lower 95%-prediction band, and the adding of a vertical line at the point where the horizontal line crosses the lower 95%-prediction band. The obtained intersection point on the fitted linear-exponential curve is then regarded as the LOD. Results of the assessment of the LOD for the individual tracers are shown in Table 4.

The samples used according to embodiments of the present invention are not necessarily of human origin.

In other embodiments, the sample derives from human blood, in particular plasma of human blood. According to these embodiments, also a method for determining metabolism of a target substance, including glucose, by high-resolution mass spectrometry may be provided. Thereby, the method may comprise administering at least one tracer molecule to a living organism, each one of the at least one tracer molecule having a chemical structure and an elemental composition of the target substance. The method may further comprise extracting at least one sample from a body fluid of the living organism and analyzing the at least one sample using high-resolution mass spectrometry, to detect an enrichment of the at least one tracer molecule in the sample. In particular, more than one tracer molecule may have been administered and more than one tracer molecule may then be analyzed to detect the respective enrichment. One or more of the tracer molecules may have been supplied to a blood stream of the living organism and one or more of the tracer molecules may have been supplied to a digestive tract of the living organism. The enrichment of one or more tracer molecules may be determined in dependence of time elapsed after administering the respective target molecules to the living organism. However, the method for determining the enrichments of the tracers may also be performed without the sample being of human origin.

The invention claimed is:

1. A method for determining, in a sample, enrichments of a first and at least one second stable-labeled tracer of at least one target substance including glucose, the first tracer and the second tracer being generated by isotopic or bioisosteric substitution in the target substance, the method comprising:
   ionizing the first tracer, the second tracer and the target substance of the sample;
   measuring intensities of ions deriving from the target substance, of ions deriving from the first tracer and of ions deriving from the second tracer using a high-resolution mass analyzer;
   calculating an enrichment of the first tracer from a first ratio of the intensity of the ions deriving from the first tracer to the intensity of the ions deriving from the target substance employing a first calibration curve being independent of enrichments of each of the at least one second tracer,
   wherein the high-resolution mass analyzer is operated so as to resolve an ion peak deriving from a tracer and having a width $\Delta(m/z)$ at half maximum peak height equal to or smaller than $1 \times 10^{-2}$.

2. The method according to claim 1, further comprising:
   calculating an enrichment of the second tracer from a second ratio of the intensity of the ions deriving from the second tracer to the intensity of the ions deriving from the target substance employing a second calibration curve being independent of the enrichment of the first tracer.

3. The method according to claim 1, wherein the high-resolution mass analyzer is operated at a mass resolving power equal to or greater than 75000 when a $^{13}$C-, $^2$H-, and/or $^{18}$O-labeled tracer of glucose is present in the sample, and equal to or greater than 200000 when a $^{17}$O-labeled tracer of glucose is also present in the sample,
   wherein the mass resolving power is calculated as the quotient of the m/z value of 180 and the width of the ion peak at half maximum peak height.

4. The method according to claim 1, further comprising:
   at least partly separating of undesired substances contained in a raw sample by performing chromatography to obtain the sample.

5. The method according to claim 1, wherein a first mass value of the mass of the first tracer differs from a second mass value of the mass of the second tracer by between 2 mDa and 10 mDa.

6. The method according to claim 1, wherein the first calibration curve is representable by a first mathematical function that relates values of the first calibration ratios of ion intensities to enrichments of the first tracer.

7. The method according to claim 1, wherein the first calibration curve is completely independent of the enrichment of any of the at least one second tracer,
wherein one of the following holds:
the first tracer contains a $^{13}$C-substitution and the at least one second tracer comprises at least one of: a $^2$H- and/or $^{17}$O- and/or $^{18}$O-substitution
the first tracer contains a $^2$H-substitution and the at least one second tracer contains at least one of: a $^{13}$C- and/or $^{17}$O- and/or $^{18}$O-substitution
the first tracer contains a $^{17}$O-substitution and the at least one second tracer contains at least one of: a $^{13}$C- and/or $^2$H- and/or $^{18}$O-substitution and
the first tracer contains a $^{18}$O-substitution and the at least one second tracer contains at least one of: a $^{13}$C- and/or $^2$H- and/or $^{17}$O-substitution.

8. The method according to claim 1, wherein the first calibration curve is practically independent of the enrichment of any of the at least one second tracer, wherein a nominal mass difference between the first tracer and the second tracer is at least 1 Da,
wherein one of the following holds:
the first tracer contains a $^2$H-substitution and the at least one second tracer contains another $^2$H-substitution,
the first tracer contains a $^{17}$O-substitution and the at least one second tracer contains another $^{17}$O-substitution,
the first tracer contains a $^{18}$O-substitution and the at least one second tracer contains another $^{18}$O-substitution.

9. The method according to claim 1, wherein the first tracer contains a first isotopic substitution including one of a $^2$H-, $^{17}$O-, $^{13}$C-substitution,
wherein a first mathematical function representing the first calibration curve is obtained by the following steps, if no other tracer containing the first isotopic substitution is present in the sample, or if the nominal mass difference between tracers containing the first isotopic substitution is at least 1 Da or 2 Da, if the first isotopic substitution is a $^{13}$C-substitution:
analyzing calibration samples containing known first enrichments of the first tracer using the high-resolution mass analyzer to obtain first calibration ratios;
fitting a mathematical function to the known first enrichment and associated first calibration ratios,
wherein the mathematical function is linear or has the following form:

$TTR = a + b\ RI + c\ d^{RI}$ where a, b, c, and d are fitting parameters, TTR is the first enrichment, and RI is the first calibration ratio.

10. The method according to claim 1, further comprising:
resolving, in a mass spectrum, a first ion peak caused by the first tracer from a second ion peak caused by the second tracer;
deriving the enrichment of the first tracer based on the first ion peak and an ion peak caused by the target substance; and
deriving the enrichment of the second tracer molecule based on the second ion peak and the ion peak caused by the target substance.

11. The method according to claim 1, wherein the target substance includes at least one further target molecule, the method comprising:
ionizing a further first tracer of the further target molecule and ionizing the further target molecule of the sample;
measuring intensities of ions deriving from the further target molecule and of ions deriving from the further first tracer using of the high-resolution mass analyzer;
calculating an enrichment of the further first tracer from a further first ratio of the intensity of the ions deriving from the further first tracer to the intensity of the ions deriving from the further target molecule employing a further first calibration curve being independent of an enrichment of any other tracer of the further target molecule.

12. The method according to claim 1, wherein at least one of the target substance and the further target molecule comprises one of:
a carbohydrate;
a carbohydrate derivative;
a sugar alcohol;
a ketone body;
a lipid;
an alcohol;
water.

13. The method according to claim 1, wherein at least one of a tracer of the target substance and a tracer of the further target molecule is added as an internal standard to the sample and, by taking the resulting tracer enrichment level and the known amount of added tracer, at least one of the concentration of the target substance and the concentration of the further target molecule in the sample are calculated.

14. The method according to claim 1, wherein a number of ions deriving from the tracers and entering the mass analyzer is maintained below the coalescence threshold by adjusting the mass scan window to a m/z range of one of 179 to 186 and 100 to 350 and lowering the automatic gain control to a value of one of between $10^4$ and $10^6$ and between $10^3$ and $10^4$.

15. The method according to claim 1, wherein an intensity of the ion peak deriving from the target substance is maintained above a threshold level of $1.0 \times 10^7$ arbitrary units by at least one of increasing the amount of sample injected into the chromatograph to a value between 1 and 3 μl, and decreasing the mass scan window to a m/z range of one of 100 to 350 and of 179 to 186, and increasing the automatic gain control to a value of one of between $10^3$ and $10^4$ and between $10^4$ and $10^6$.

16. The method according to claim 7,
wherein the first tracer and the second tracer have a same nominal mass.

17. The method according to claim 13, wherein the carbohydrate is one of a monosaccharide, a disaccharide, an oligosaccharide, a polysaccharide.

18. The method according to claim 1, wherein the target substance is glucose.

* * * * *

UNITED STATES PATENT AND TRADEMARK OFFICE
CERTIFICATE OF CORRECTION

PATENT NO. : 11,454,616 B2
APPLICATION NO. : 16/624841
DATED : September 27, 2022
INVENTOR(S) : Werner Regittnig et al.

Page 1 of 1

It is certified that error appears in the above-identified patent and that said Letters Patent is hereby corrected as shown below:

In the Claims

Claim 9, Column 23, Line 39, after "$^{17}$O-," insert --$^{18}$O-,--.

Signed and Sealed this
Twenty-fourth Day of January, 2023

Katherine Kelly Vidal
*Director of the United States Patent and Trademark Office*